United States Patent
Hayes et al.

(10) Patent No.: US 9,320,444 B2
(45) Date of Patent: Apr. 26, 2016

(54) PATIENT SUPPORT APPARATUS WITH PATIENT INFORMATION SENSORS

(71) Applicant: Stryker Corporation, Kalamazoo, MI (US)

(72) Inventors: Michael Joseph Hayes, Kalamazoo, MI (US); David Terrance Becker, Grand Rapids, MI (US); Aaron Douglas Furman, Kalamazoo, MI (US); Brandon J. Buckingham, Kalamazoo, MI (US); Michael W. Steffler, Kalamazoo, MI (US); Richard A. Derenne, Portage, MI (US); Joshua Elmer Mix, Portage, MI (US); Annie Désaulniers, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 88 days.

(21) Appl. No.: 14/212,367

(22) Filed: Mar. 14, 2014

(65) Prior Publication Data

US 2014/0266733 A1    Sep. 18, 2014

Related U.S. Application Data

(60) Provisional application No. 61/791,117, filed on Mar. 15, 2013.

(51) Int. Cl.
*G08B 23/00* (2006.01)
*A61B 5/0205* (2006.01)
(Continued)

(52) U.S. Cl.
CPC .............. *A61B 5/0205* (2013.01); *A61G 7/05* (2013.01); *A61G 7/057* (2013.01); *A61B 5/4809* (2013.01);
(Continued)

(58) Field of Classification Search
CPC .......... G08B 21/02; A61G 7/05; A61B 5/0205

USPC ................... 340/573.4, 665–667; 600/484
See application file for complete search history.

(56) References Cited

U.S. PATENT DOCUMENTS 5,276,432 A    1/1994    Travis
6,239,706 B1   5/2001    Yoshiike et al.
(Continued)

FOREIGN PATENT DOCUMENTS

EP    2053969 B1       5/2012
WO    9427544          12/1994
WO    2012/122002 A1   9/2012

OTHER PUBLICATIONS

PCT International Search Report regarding Application No. PCT/US2014/26030 filed on Mar. 13, 2014, a counterpart of U.S. Appl. No. 14/212,367.
(Continued)

*Primary Examiner* — Eric Blount
(74) *Attorney, Agent, or Firm* — Warner Norcross & Judd LLP

(57) ABSTRACT

A patient support apparatus includes multiple sensors used to monitor aspects of a patient positioned on a support surface of the patient support apparatus. The outputs from the sensors are used, alone or in combination with other signals, to perform any one or more of the following: distinguishing between new and old patients entering onto the support surface; automatically zeroing a scale system on the support apparatus; distinguishing between objects and humans positioned on the support surface; determining if a patient is sleeping or awake; monitoring and characterizing movement levels of the patient; recording for subsequent display a log of likely events regarding the support surface; proposing identifications of objects added to or removed from the support surface; automatically re-arming a patient exit alert system; recording force outputs prior to and during a patient exit from the support apparatus; and transmitting the recorded force outputs to a remote location.

38 Claims, 19 Drawing Sheets

(51) Int. Cl.
*A61G 7/05* (2006.01)
*A61G 7/057* (2006.01)
*A61B 5/00* (2006.01)

(52) U.S. Cl.
CPC ............. *A61B 5/6891* (2013.01); *A61B 5/6892* (2013.01); *A61B 2505/00* (2013.01); *A61G 2007/0527* (2013.01); *A61G 2203/36* (2013.01)

(56) References Cited

U.S. PATENT DOCUMENTS

| | | | |
|---|---|---|---|
| 6,469,263 | B1 | 10/2002 | Johnson |
| 7,081,091 | B2 * | 7/2006 | Merrett ................ A61B 5/0205 128/920 |
| 7,253,366 | B2 | 8/2007 | Bhai |
| 7,699,784 | B2 * | 4/2010 | Wan Fong .......... A61B 5/02444 600/481 |
| 8,381,336 | B2 | 2/2013 | Kazuno et al. |
| 8,403,865 | B2 * | 3/2013 | Halperin ................ A61B 5/113 600/529 |
| 8,413,271 | B2 * | 4/2013 | Blanchard ................ A61G 7/00 5/173 |
| 8,466,801 | B2 | 6/2013 | Hayes et al. |
| 8,674,826 | B2 | 3/2014 | Becker et al. |
| 2007/0156031 | A1 * | 7/2007 | Sullivan ................ G08B 21/02 600/300 |
| 2007/0174964 | A1 | 8/2007 | Lemire et al. |
| 2007/0268147 | A1 | 11/2007 | Bhai |
| 2008/0169931 | A1 * | 7/2008 | Gentry ................ A61B 5/1113 340/573.1 |
| 2008/0172789 | A1 | 7/2008 | Elliot et al. |
| 2011/0046498 | A1 * | 2/2011 | Klap .................... A61B 5/0205 600/534 |
| 2011/0068935 | A1 | 3/2011 | Riley et al. |
| 2011/0144548 | A1 | 6/2011 | Elliott et al. |
| 2011/0156915 | A1 | 6/2011 | Brauers et al. |
| 2013/0205501 | A1 | 8/2013 | Robertson et al. |
| 2013/0342351 | A1 | 12/2013 | Riley et al. |
| 2014/0039351 | A1 | 2/2014 | Mix et al. |

OTHER PUBLICATIONS

PCT International Written Opinion regarding Application No. PCT/US2014/26030 filed on Mar. 13, 2014, a counterpart of U.S. Appl. No. 14/212,367.

* cited by examiner

PATIENT SUPPORT APPARATUS WITH PATIENT INFORMATION SENSORS

CROSS-REFERENCE TO RELATED APPLICATIONS

The present application claims priority to U.S. provisional patent application Ser. No. 61/791,117 filed Mar. 15, 2013 by applicants Michael Hayes et al. and entitled PATIENT SUPPORT APPARATUS WITH PATIENT INFORMATION SENSORS, the complete disclosure of which is hereby incorporated herein by reference.

BACKGROUND

The present invention relates to patient support apparatuses, such as beds, stretchers, cots, recliners, operating tables, and the like.

SUMMARY OF THE INVENTION

The various embodiments of the present invention provide improved patient support apparatuses that, in some embodiments, provide improved functionality, ease of use, and/or improved features. The improved patient support apparatuses include a plurality of patient information sensors that are able to sense information about patients or objects positioned on a support surface of the patient support apparatus. Such patient information sensors include force sensors adapted to detect downward forces exerted on the patient support apparatus by the patient and/or objects, as well as other patient information sensors. The outputs from the patient information sensors are used, either alone or in combination with other signals, to perform any one or more of the following, depending upon the various embodiments: distinguishing between new and old patients entering onto the support surface; automatically zeroing a scale system on the support apparatus; distinguishing between objects and humans positioned on the support surface; determining if a patient is sleeping or awake; monitoring and characterizing movement levels of the patient; recording for subsequent display a log of likely events regarding the support surface; proposing identifications of objects added to or removed from the support surface; automatically re-arming a patient exit alert system; recording force outputs prior to and during a patient exit from the support apparatus; and transmitting the recorded force outputs to a remote location. In some embodiments, real time, or near real time, monitoring of weight readings are taken, recorded, analyzed, and the results of the analysis are made available for display to a caregiver, or forwarded to a healthcare computer network where they may be used by other applications or servers (e.g. an electronic medical records server).

According to one aspect, a patient support apparatus is provided that includes a base, a frame supported on the base, a patient support surface, a plurality of force sensors, and a controller. The patient support surface is adapted to support a patient thereon, and the plurality of force sensors are coupled to the frame and adapted to output signals corresponding to downward forces exerted on the patient support surface. The controller is in communication with the plurality of force sensors and adapted to analyze the signals to determine if the signals are indicative of a prior patient having re-entered onto the patient support surface, or a new patient having entered on the patient support surface.

According to other aspects, the patient support apparatus includes a user interface in communication with the controller, wherein the controller provides an indication to a caregiver via the user interface when the controller determines that the signals are indicative of a new patient having entered onto the patient support surface. The user interface may be configured to prompt the caregiver to confirm or reject that the new patient did in fact enter onto the patient support surface.

A vital signs sensor is positioned on the patient support apparatus in some embodiments. The vital sign sensor detects a vital sign of a patient when the patient is supported on the patient support surface. The controller communicates with the vital sign sensor and uses outputs from the vital sign sensor in determining if the signals are indicative of the prior patient or the new patient having entered onto the patient support surface. The vital sign sensor may be incorporated into a pressure sensing mat positioned on the patient support surface wherein the pressure sensing mat includes an array of pressure sensors that able to detect at least one vital sign of a patient supported on the patient support surface. In addition, or alternatively, the vital sign sensor may comprise an air pressure sensor adapted to detect changes in air pressure within an inflatable bladder contained within a mattress supported on the patient support surface. The vital sign sensor is adapted to detect a patient's heart rate and/or respiration rate, although other vital signs may additionally or alternatively be detected.

In other aspects, when the controller determines that the signals are indicative of a new patient having entered onto the patient support surface, the controller prompts the caregiver to confirm or reject that a new patient did in fact enter onto the patient support surface. The prompting takes place in conjunction with a user interface on the patient support apparatus, which may include a display. The controller is further adapted to prompt a caregiver—when a new patient is detected—to clear any old data stored in a memory on the patient support apparatus relating to the prior patient, and to enter new data relating to the new patient. The new data includes any one or more of the following: a height of the new patient, a weight of the new patient, a name of the new patient, a fall risk assessment of the new patient, a bed sore assessment of the new patient, a turn protocol for the new patient, an alert setting for the new patient, a body-mass index for the new patient, or an infection risk assessment for the new patient.

In other aspects, the force sensors repetitively output signals corresponding to the downward forces and the controller uses the repetitively output signals to establish a baseline level of forces. The controller determines that the signals are indicative of the prior patient having entered onto the patient support surface if the signals exceed the baseline level of forces by an amount substantially equal to a previously stored weight of the prior patient. If the signals exceed the baseline level of forces by an amount that is different from the previously stored weight of the patient by more than a threshold value, the controller determines that a new patient has entered the patient support apparatus.

In some aspects, the plurality of force sensors repetitively output signals corresponding to the downward forces, and the controller uses the repetitively output signals to establish a baseline level of forces. The controller determines that the signals are indicative of a new patient having entered onto the patient support surface only if both (a) the signals exceed the baseline level of forces by an amount not substantially equal to a previously stored weight of the prior patient, and (b) the vital sign sensor is able to detect a vital sign of a patient positioned on the patient support surface.

The controller records a time when signals indicative of either the new patient or the prior patient having entered onto the patient support surface are detected, in some embodiments. In other embodiments, the controller records the signals over a time period prior to detecting the signals indicative of either the prior patient or the new patient having entered onto the patient support surface, determines a baseline level of forces from the signals recorded over the time period, and allows a caregiver to accept the baseline level of forces as a tare weight.

The controller may further analyze the signals to determine if the signals are indicative of a non-human object placed on the patient support surface. The controller may further propose an identification of the non-human object based at least partially upon the signals from the force sensors, and the controller may prompt the caregiver to confirm or reject the proposed identification of the non-human object.

An exit alert system can be coupled to the patient support apparatus and adapted to issue an alert if a patient on the patient support surface moves beyond a threshold amount while the exit alert system is armed. When included, the controller is adapted to automatically re-enable the exit alert system if the signals are indicative of the prior patient having re-entered the patient support surface and the patient exit alert system was previously armed.

According to another embodiment, a patient support apparatus is provided that includes a base, a frame supported on the base, a patient support surface, a plurality of force sensors, and a controller. The patient support surface is adapted to support a patient thereon. The force sensors are coupled to the frame and adapted to output signals corresponding to downward forces exerted on the patient support surface. The controller is in communication with the plurality of force sensors and adapted to record outputs from the plurality of force sensors over time, to determine if a likely event with respect to the patient support surface has occurred, and to prompt a caregiver to confirm or reject that the likely event has actually occurred.

In other aspects, the likely event includes any one or more of the following: (a) a new patient has entered the patient support surface, (b) a prior patient has re-entered the patient support surface; (c) a non-human object has been placed on the patient support surface, (d) a person has or is leaning on the patient support surface, and (e) a non-human object has been removed from the patient support apparatus.

The controller may be adapted to time stamp each likely event and to display a time corresponding to each likely event when prompting the caregiver to confirm or reject that the likely event has actually occurred.

In another embodiment, the controller determines a baseline weight sensed by the sensors prior to the likely event, determines a second weight sensed by the sensors after the likely event, and displays a difference between the baseline weight and the second weight on a display supported on the patient support apparatus. The controller uses the difference between the baseline weight and the second weight to characterize the likely event and display the characterization. The controller prompts a caregiver to accept or reject the displayed characterization. The characterization includes any one or more of the following: (a) a new patient has entered the patient support surface, (b) a prior patient has re-entered the patient support surface; (c) a non-human object has been placed on the patient support surface, (d) a person has or is leaning on the patient support surface, and (e) a non-human object has been removed from the patient support apparatus. If the controller characterizes the likely event as one of (c) or (e), the controller uses the difference between the baseline weight and the second weight to display a potential identification of the non-human object. The controller prompts the caregiver to accept or reject the displayed possible identification of the non-human object.

According to other aspects, the controller uses at least one vital sign detected by the force sensors to characterize the likely event and display the characterization. If the controller detects either a cessation or a commencement of vital sign signals, the controller determines that the signals from the plurality of force sensors are likely indicative of a human moving onto or off the patient support surface.

According to another embodiment, a patient support apparatus is provided that includes a base, a frame supported on the base, a patient support surface, a plurality of force sensors, and a controller in communication with the plurality of force sensors. The force sensors are coupled to the frame and adapted to output signals corresponding to downward forces exerted on the patient support surface. The controller monitors the signals from the plurality of force sensors and analyzes the signals to determine if the signals are indicative of a non-human object moving onto or off the patient support surface.

In other aspects, the controller generates a proposed identification of the non-human object and displays the proposed identification on a display coupled to the controller. The proposed identification is based upon a change in weight detected by the plurality of force sensors before and after the non-human object is moved onto or off of the patient support surface. The controller is further adapted to use the display to prompt a caregiver to accept or reject the proposed identification of the non-human object. The proposed identification of the non-human object includes at least one of a medical device, bedding, and a pillow. The proposed identification of the medical device includes, in at least one embodiment, an identification of a ventilator and a pump.

The plurality of force sensors may be load cells integrated into the patient support apparatus.

According to yet another embodiment, a patient support apparatus is provided that includes a base, a frame, a patient support surface, a plurality of force sensors, a display, and a controller. The plurality of force sensors are coupled to the frame and adapted to output signals corresponding to downward forces exerted on the patient support surface. The controller is in communication with the plurality of force sensors and the display, and the controller is adapted to categorize changes in the outputs and to record a time when each of the categorized changes occurs. The controller is further adapted to display information relating to the categorized changes on the display.

According to still another embodiment, a patient support apparatus is provided that includes a base, a frame, a patient support surface, a plurality of force sensors, a display, and a controller. The plurality of force sensors are coupled to the frame and adapted to output signals corresponding to downward forces exerted on the patient support surface. The controller is in communication with the plurality of force sensors and the display, and the controller is adapted use the signals from the plurality of force sensors to propose on the display an identification of a non-human object moving onto or off the patient support surface.

According to another embodiment, a patient support apparatus is provided that includes a base, a frame, a patient support surface, a vital sign sensor, an exit alert system, and a controller. The vital sign sensor is supported on the frame and is adapted to output signals corresponding to a vital sign of a patient supported on the patient support surface. The exit alert system is coupled to the patient support apparatus, and the exit alert system is adapted to issue an alert if a patient on the patient support surface moves beyond a threshold amount while the exit alert system is armed. The controller is in communication with the vital sign sensor and adapted to use the signals from the vital sign sensor in determining whether to automatically re-arm the exit alert system after the exit alert system has been disarmed.

According to other aspects, the vital sign sensor may include a plurality of force sensors coupled to the frame and adapted to output signals corresponding to downward forces exerted on the patient support surface. The force sensors may be load cells. The load cells may be integrated into a scale system adapted to measure a weight of a patient positioned on the patient support surface. Still further, the exit alert system may use the same, or at least some common, components as those of the vital sign sensor. In other embodiments, the vital sign sensor is a fluid pressure sensor positioned inside an inflatable bladder contained within a mattress supported on the patient support surface. The fluid pressure sensor detects changes in air pressure inside the inflatable bladder corresponding to one or both of a patient's heart rate or respiration rate.

According to another embodiment, a patient support apparatus is provided that includes a base, a frame, a patient support surface, a scale system, and a controller. The scale system includes a plurality of force sensors coupled to the frame and adapted to output signals corresponding to weight exerted on the patient support surface. The controller communicates with the scale system and is adapted to automatically record a weight sensed by the scale system prior to a patient entering the patient support surface and to allow a caregiver to accept the recorded weight as a tare weight.

The controller may be further adapted to display the recorded weight on a display coupled to the patient support apparatus. The controller may prompt the caregiver to accept or reject the recorded weight as a tare weight. If the caregiver accepts the recorded weight as a tare weight, the controller subtracts the tare weight from a weight reading taken after the patient enters onto the patient support surface. A user interface may be provided that allows a caregiver to view the recorded weight even after the caregiver accepts the recorded weight as the tare weight.

According to still another embodiment, a patient support apparatus is provided that includes a base, a frame, a patient support surface, a plurality of force sensors, a display, and a controller. The plurality of force sensors are coupled to the frame and adapted to output signals corresponding to downward forces exerted on the patient support surface. The controller is in communication with the plurality of force sensors and the display, and the controller is adapted to classify the signals from the plurality of force sensors into a plurality of different levels of movement by a patient supported on the patient support surface. The controller further displays the different levels of movement on the display.

The controller may further record a duration of each of the plurality of different levels of movement and display them on the display. The levels of movement may include a high level of activity, a moderate level of activity, and a low level of activity, as well as other levels of activity. The controller is further able to record starting and ending times for each of the plurality of different levels of movement. The recorded starting and ending times are displayable on the display.

The controller can also be configured to calculate a cumulative amount of time a patient spends engaging in each of the plurality of levels of movement. One level of movement may correspond to the patient being asleep.

One or more vital sign sensors may also be included that, in conjunction with the plurality of force sensors, are used by the controller to classify whether a patient supported on the patient support apparatus is sleeping or not. The vital sign sensors include sensors that detect a patient's respiration rate and/or heart rate. The vital sign sensors may utilize the plurality of force sensors, and/or the vital sign sensors may be incorporated into a mattress supported on the patient support surface. As yet another alternative, the vital sign sensor may be incorporated into a flexible pressure sensing mat having an array of pressure sensors, wherein the pressure sensing mat is positioned between the patient support surface and a patient supported thereon, and the pressure sensing mat is in communication with the controller.

The controller may further be adapted to issue an alert regarding potential bed sore development if the patient remains at a low level of movement for more than a predetermined amount of time. The controller allows the caregiver to select the predetermined amount of time. The controller further records cumulative durations of time for each of the plurality of different levels of movement and allows a caregiver to select a range of time over which to display the cumulative durations.

According to yet another embodiment, a patient support apparatus is provided that includes a base, a frame, a patient support surface, a plurality of force sensors, and a controller. The plurality of force sensors are coupled to the frame and adapted to output signals corresponding to downward forces exerted on the patient support surface. The controller is in communication with the plurality of force sensors and adapted to use the signals from the plurality of force sensors to estimate whether a patient supported on the patient support surface is asleep or not.

In some embodiments, the plurality of force sensors include a plurality of load cells that are incorporated into a scale system, and the scale system is adapted to determine both a level of movement of the patient positioned on the patient support surface, and at least one vital sign of the patient positioned on the patient support surface. The at least one vital sign includes a patient's respiration rate and/or heart rate. The controller may be configured to use both the level of movement of the patient and the vital sign when estimating whether the patient supported on the patient support surface is asleep or not.

According to another embodiment, a patient support apparatus is provided that includes a base, a frame, a patient support surface, an exit alert system, and a controller. The exit alert system is adapted to issue an alert if a patient on the patient support surface either completely exits the patient support, or otherwise makes initial movements toward exiting the bed while the exit alert system is armed. The controller is in communication with the exit alert system and adapted to record a time when a patient positioned on the patient support surface exits the patient support surface, or otherwise triggers the exit alert system, regardless of whether or not the exit alert system is armed or not.

A display may be included that is in communication with the controller, and the controller may be adapted to display the time when the patient positioned on the patient support surface exited the patient support. The controller may further be adapted to record how long the patient remains off the patient support surface after exiting the patient support surface. The exit alert system may include a plurality of force sensors adapted to detect downward forces exerted on the patient support surface. The force sensors may comprise load cells integrated into the patient support apparatus. The controller, in some embodiments, is adapted to record outputs of the load cells prior to, and during, the exiting of the patient from the patient support surface. The recorded outputs are stored for transmission to a location remote from the patient support apparatus for analysis. Alternatively, or additionally, the controller is able to use the recorded outputs of the load cells to analyze future outputs of the load cells. Such analysis may include analyzing future outputs of the load cells for similarities to the recorded outputs. Such analysis may also involve looking for patterns in the recorded outputs and using any discovered patterns to analyze future outputs of the load cells in order to predict when a patient may be about to exit the patient support apparatus. Such prediction may occur prior to an alert being triggered by the exit alert system.

According to another embodiment, a patient support apparatus is provided that includes a base, a frame, a patient support surface, an exit alert system, and a controller. The exit alert system is adapted to issue an alert if a patient on the patient support surface moves beyond a threshold amount while the exit alert system is armed. The exit alert system includes a plurality of force sensors coupled to the frame and adapted to output signals corresponding to downward forces exerted on the patient support surface. The controller is in communication with the plurality of force sensors and the transceiver, and the controller records outputs from the force sensors when a patient exits the patient support surface and transmits the recorded outputs to a remote location, regardless of whether or not the exit alert system is armed.

The transmission of the recorded outputs to the remote location may take place wirelessly via a WiFi link (IEEE 802.11). The controller may record outputs from the force sensors both prior to, and during, the patient exit, and such recordings may be transmitted to the remote location. The plurality of force sensors may be adapted to measure a weight of a patient positioned on the patient support surface, and/or the plurality of force sensors may be load cells. The controller may be further adapted to receive instructions from the remote location to modify the exit alert system in a manner that is based at least partially upon the recorded outputs transmitted to the remote location.

According to yet another embodiment, a patient support apparatus is provided that includes a base, a frame, a patient support surface, a plurality of force sensors, and a controller. The plurality of force sensors are coupled to the frame and adapted to output signals corresponding to downward forces exerted on the patient support surface. The controller is in communication with the plurality of force sensors, and the controller is adapted to use the signals from the plurality of force sensors to estimate whether a patient supported on the patient support surface has turned or not.

According to other aspects, the controller records a time at which each turn is estimated to have occurred, as well as a duration of time between each turn. The controller may also determine which way a patient has turned, such as, but not limited to, from the patient's back to the patient's right side, from the patient's back to the patient's left side, from the patient's left side to the back, from the patient's right side to the back, and/or from one of the patient's right or left sides to the other of the patient's right or left sides.

According to yet another embodiment, a patient support apparatus is provided that includes a base, a frame, a patient support surface, a scale system, a user interface, and a controller. The scale system is coupled to the frame and adapted to output weight signals corresponding to weight exerted on the patient support surface. The user interface allows a caregiver to use the scale system to weigh a patient positioned on the patient support surface. The controller is in communication with the scale system and the user interface, and the controller is adapted to use the weight signals to automatically record a first weight prior to a patient entering onto the patient support surface so that a patient weight may be determined by subtracting the first weight from a second weight recorded after a patient has entered onto the patient support surface.

A display may further be included that is adapted to display any one or more of the first weight, second weight, and/or patient weight.

In any of the embodiments discussed herein, the patient support apparatus may be one of a bed, a stretcher, a cot, a recliner, or an operating table.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE EMBODIMENTS

Figure 1:
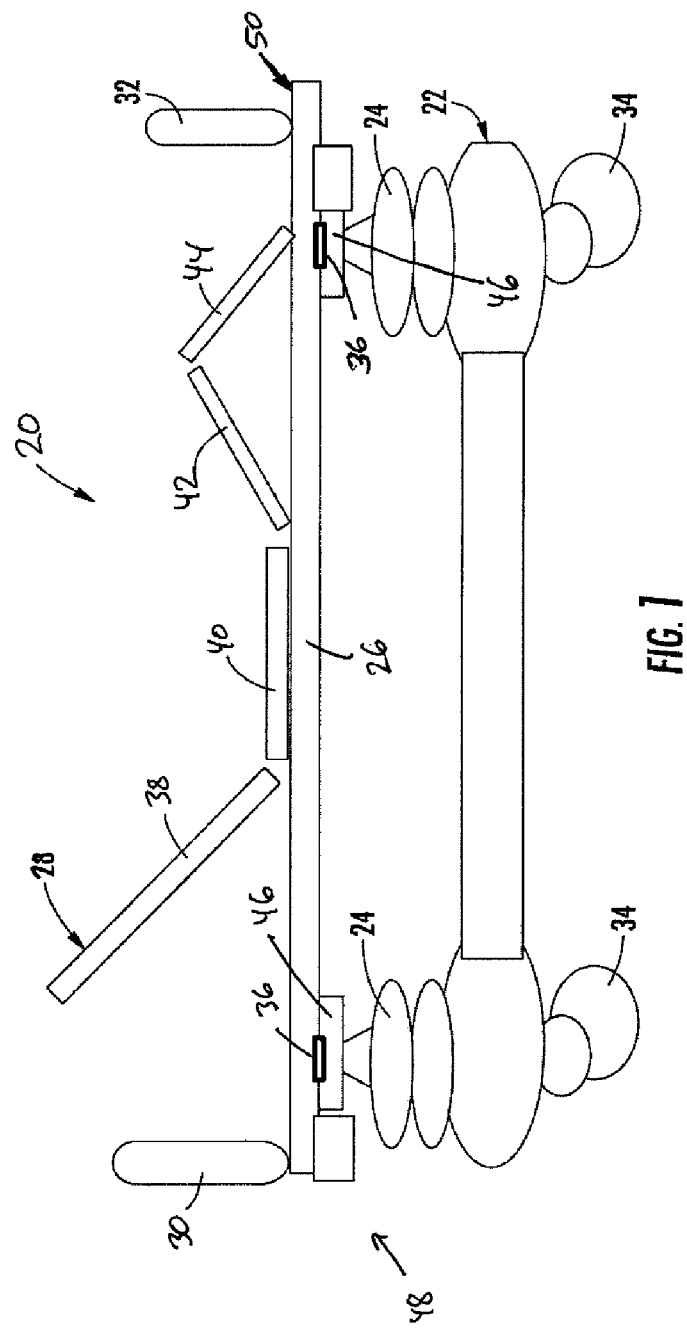
FIG. 1 is a side, elevational diagram of the physical construction of a patient support apparatus that may incorporate any one or more of the various features and functions described herein.

The inventive features and functions described herein are applicable to patient support apparatuses, such as beds, cots, stretchers, operating tables, recliners, and the like. FIG. 1 illustrates in diagrammatic form the general components that are commonly found in some of these patient support apparatuses, particularly when the support apparatuses are beds or stretchers. More particularly, FIG. 1 illustrates a patient support apparatus 20 that includes a base 22, a pair of elevation adjustment mechanisms 24, a frame or litter assembly 26, a patient support surface or deck 28, a headboard 30, and a footboard 32. Base 22 includes a plurality of wheels 34 that can be selectively locked and unlocked so that, when unlocked, patient support apparatus 20 is able to be wheeled to different locations. Elevation adjustment mechanisms 24 are adapted to raise and lower frame 26 with respect to base 22. Elevation adjustment mechanisms 24 may be hydraulic actuators, electric actuators, or any other suitable device for raising and lowering frame 26 with respect to base 22. In some embodiments, elevation adjustment mechanisms 24 operate independently so that the orientation of frame 26 with respect to base 22 may also be adjusted.

Frame 26 provides a structure for supporting patient support surface 28, headboard 30, and footboard 32. Patient support surface 28 provides a surface on which a mattress, or other soft cushion, is positionable so that a patient may lie and/or sit thereon. Patient support surface 28 is made of a plurality of sections, some of which are pivotable about generally horizontal pivot axes. In the embodiment shown in FIG. 1, patient support surface 28 includes a head section 38, a seat section 40, a thigh section 42, and a foot section 44. Head section 38, which is also sometimes referred to as a Fowler section, is pivotable between a generally horizontal orientation (not shown in FIG. 1) and a plurality of raised positions (one of which is shown in FIG. 1). Thigh section 42 and foot section 44 may also be pivotable, such as is shown in FIG. 1.

Patient support apparatus 20 further includes a plurality of load cells 36 positioned between an underside of frame 26 and support structures 46 coupled to elevation adjustment mechanism 24. While only two load cells 36 are visible in FIG. 1, patient support apparatus 20 includes four load cells, two positioned at a head end 48 of support apparatus 20 and another two positioned at a foot end 50 of support apparatus 20. Load cells 36 are any conventional load cells, or similar force measuring sensors, that are positioned to detect the amount of downward force exerted by patient support deck 28, and any objects, patient(s), and/or other persons that are exerting downward forces on support deck 28, whether due to gravity or due to other causes. The physical arrangement of load cells 36 is, in some embodiments, the same as that found in many conventional hospital beds. For example, in one embodiment, the position and physical construction of load cells 36 are the same as that found in the S3® bed sold by Stryker Corporation of Kalamazoo, Mich. These physical details are described in detail in the Stryker Maintenance Manual for Stryker's MedSurg Bed, Model 3002 S3, (doc. 3006-109-002 Rev D), published in 2010, the complete disclosure of which is hereby incorporated herein by reference.

Figure 2:
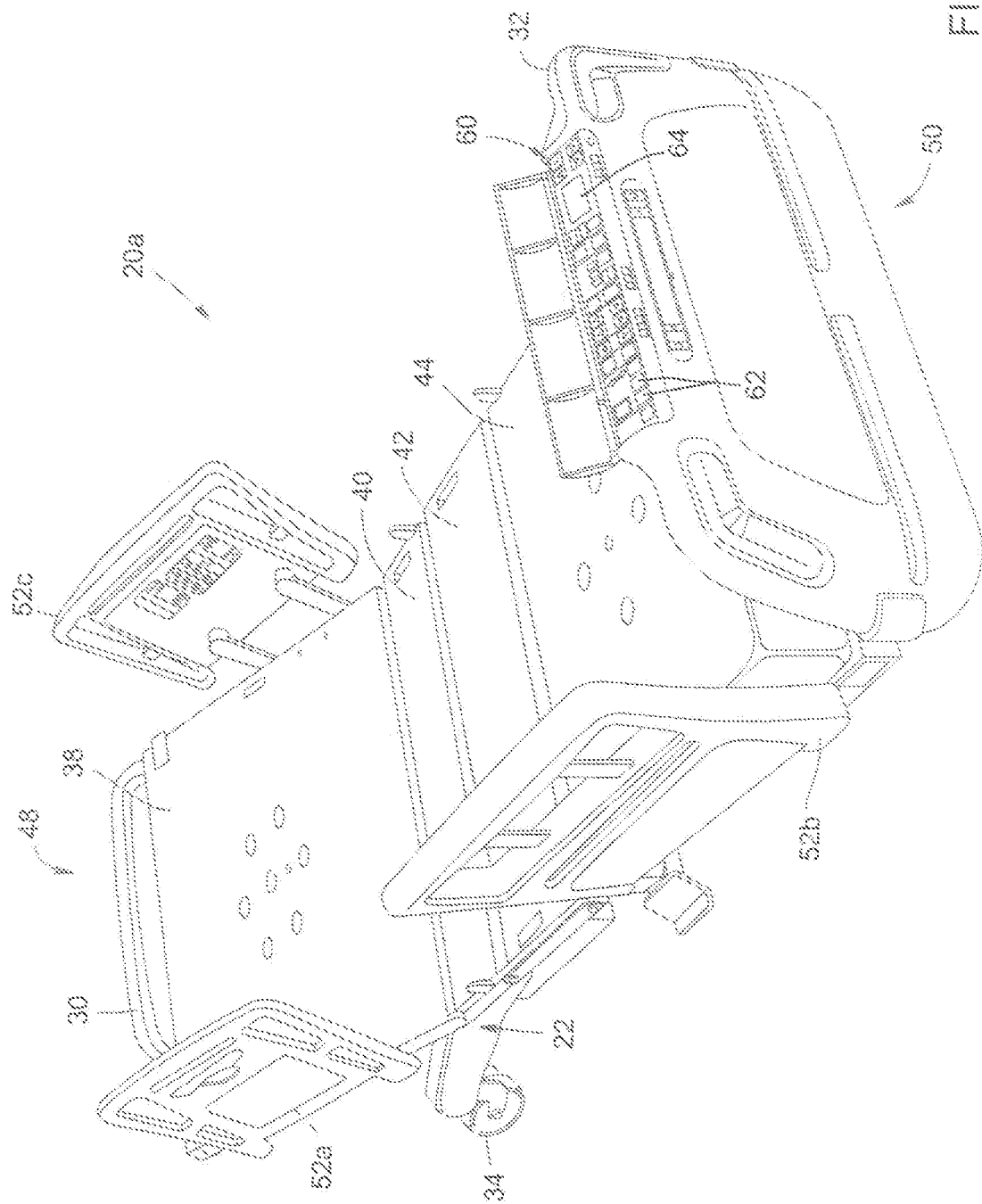
FIG. 2 is a perspective view of the physical construction of another patient support apparatus that may incorporate any one or more of the various features and functions described herein.

FIG. 2 illustrates another patient support apparatus 20a into which any of the inventive features or functions described are able to be incorporated. Patient support apparatus 20a, like support apparatus 20, includes a base 22 having a plurality of wheels 34, a frame 26 (not labeled), a pair of elevation adjustment mechanisms (not visible in FIG. 2), a support surface or deck 28, a headboard 30, and a footboard 32. Support surface 28 of patient support apparatus 20a, like that of support apparatus 20, includes four sections: a head section 38, a seat section 40, a thigh section 42, and a foot section 44. Patient support apparatus 20a, like support apparatus 20, also includes four load cells 36 (not shown) that are adapted to detect downward forces exerted by patients, other people, and/or objects on patient support surface 28.

In addition to the aforementioned components, patient support apparatus 20a includes four side rails: a right head side rail 52a, a right foot side rail 52b, a left head side rail 52c and a left foot side rail 52d (not shown). Side rails 52 are be movable between a raised position and a lowered position. In the configuration shown in FIG. 2, right head side rail 52a, right foot side rail 52b, and left head side rail 52c are shown in the raised position, while left foot side rail 52d (not visible) has been moved to the lowered position.

The physical construction of any of base 22, elevation adjustment mechanisms 24, frame 26, patient support surface 28, headboard 30, footboard 32, and/or side rails 52 may be the same as disclosed in commonly assigned, U.S. Pat. No. 7,690,059 issued to Lemire et al., and entitled HOSPITAL BED, the complete disclosure of which is incorporated herein by reference; or as disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference, or as disclosed in the aforementioned Stryker Maintenance Manual for the Model 3002 S3 MedSurg Bed, the disclosure of which was previously incorporated herein by reference. The construction of any of base 22, elevation adjustment mechanisms 24, frame 26, patient support surface 28, headboard 30, footboard 32 and/or side rails 52 may also take on forms different from what is disclosed in these documents.

Figure 3:
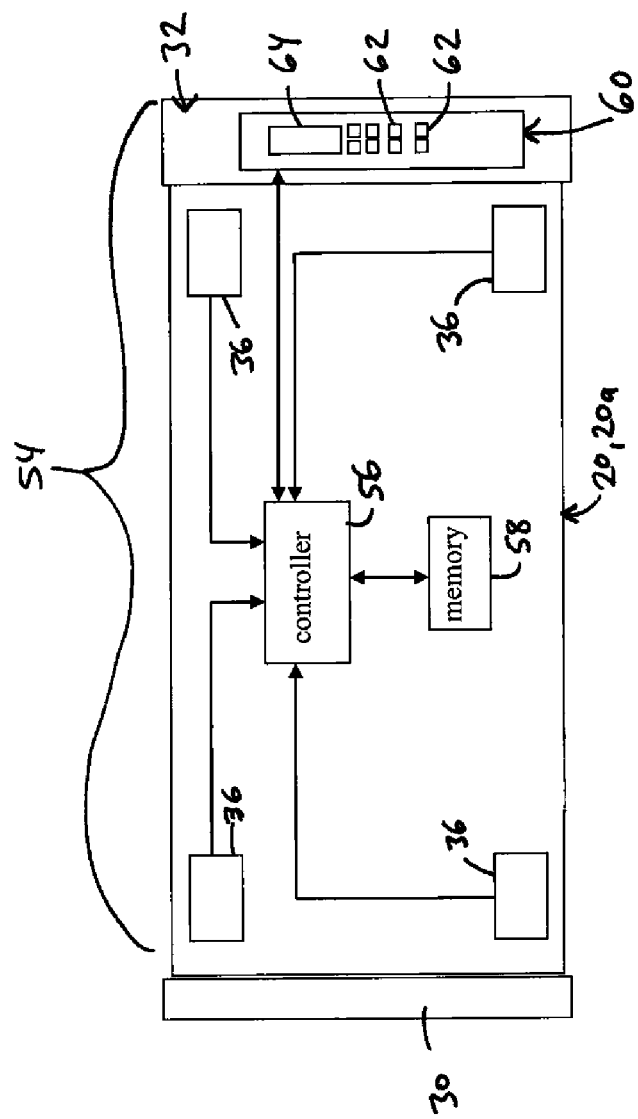
FIG. 3 is a plan view diagram of a measurement subsystem that may be incorporated into either of the patient support apparatuses of FIGS. 1 and 2.

FIG. 3 illustrates a plan view diagram of a patient support apparatus (20 or 20a) having a measurement subsystem 54. Measurement subsystem 54 may be incorporated into either or both of patient support apparatuses 20 and 20a in order to provide those patient support apparatuses with any of the features and functions described herein of measurement subsystem 54 (or the modified versions of subsystem 54 described below). Measurement subsystem 54 includes a controller 56, a memory 58 in communication with the controller 56, a user interface 60, a plurality of buttons 62, a display 64, and four force sensors or load cells 36.

The components of measurement subsystem 54 communicate with each other using conventional electronic communication techniques. In one embodiment, controller 56 communicates with memory 58, user interface 60, and load cells 36 using I-squared-C communications. Other types of serial or parallel communication can alternatively be used. In some other embodiments, different methods may be used for different components. For example, in one embodiment, controller 56 communicates with user interface 60 via a controller area network or LIN, while it communicates with memory 58 and load cells 36 using I squared C. Still other variations are possible.

User interface 60 includes a plurality of buttons 62 that a caregiver presses in order to control various features of the patient support apparatus, such as, but not limited to, raising and lowering the height of frame 26, pivoting one or more of support surface sections 28, turning on and off a brake (not shown), controlling a scale system integrated into the patient support apparatus, controlling an exit alert system integrated into the support apparatus 20 or 20a, and/or controlling other features of the patient support apparatus 20 or 20a. User interface 60 further includes display 64 integrated therein. Display 64 is a touchscreen display capable of displaying text and/or graphics and sensing the location where a user's finger touches the display, although it will be understood that display 64 could be modified to be a normal LCD display without touchscreen capabilities that uses hard or soft buttons to interact therewith, or still other types of displays.

Controller 56 includes a microcontroller that is programmed to carry out the functions described herein. It will be understood that controller 56 may be varied to include other electronic components that are programmed to carry out the functions described herein, such as, but not limited to, one or more microprocessors, microcontrollers, field programmable gate arrays, systems on a chip, volatile or nonvolatile memory, discrete circuitry, and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units.

Controller 56 is in communication with each of four load cells 36 and receives the outputs from load cells 36. Load cells 36 are positioned adjacent each corner of the patient support surface 28 and cumulatively sense the entire weight of a patient, other person, and/or objects positioned on the patient support surface 28. In one arrangement, the load cells are positioned such that one load cell 36 is positioned adjacent each corner of a load frame (not shown), and the load cells 36 detect forces exerted by a patient support frame upon the load frame (through the load cells). While the construction of the load frame and patient support frame may vary, one example is disclosed in the commonly assigned U.S. Pat. No. 7,690,059 mentioned above and incorporated herein by reference. Another example is disclosed in the Stryker Maintenance Manual for the Model 3002 S3 MedSurg Bed, which has also already been incorporated herein by reference. Other constructions of the frames and positions of the load cells may also be used.

Measurement subsystem 54 is capable of performing a variety of different functions. In some embodiments, measurement subsystem 54 is used to detect whether a patient has exited the patient support apparatus 20 or 20a, or is about to exit the patient support apparatus. One manner in which measurement subsystem 54 is able to use the load cells 36 to determine patient exit, or potential patient exit, is disclosed in commonly assigned, U.S. Pat. No. 5,276,432 issued to Travis and entitled PATIENT EXIT DETECTION MECHANISM FOR HOSPITAL BED, the complete disclosure of which is also hereby incorporated herein by reference. Other methods for using the load cells to determine patient bed exit may also be used. In the method disclosed in the U.S. Pat. No. 5,276,432, the force sensed by each load cell is determined and used, in combination with the location of each load cell, to determine the center of gravity of the forces exerted on the load cells. If the center of gravity of the forces is within a predefined region, no patient exit is presumed. If the center of gravity moves outside of a predefined region, a patient exit is presumed, and an alarm issues on the patient support apparatus 20, 20a, and/or at a remote location in communication with patient the support apparatus 20, 20a, such as a nurses' station. In some embodiments, there are multiple predefined regions, and a caregiver may be able to select which region the center of gravity has to move outside of in order to cause a patient exit alert to issue.

In addition to determining whether a patient has exited the patient support apparatus 20, 20a, or may be about to exit the patient support apparatus 20, 20a, measurement subsystem 54 is also able to determine a weight of a patient positioned on patient support apparatus 20 or 20a. Such weight measurements are based upon a summation of the total forces sensed by the load cells 48, minus the weight of the non-patient objects that exert a force on the load cells.

In the embodiment shown in FIG. 3, measurement subsystem 54 is configured to always remain on while the electrical system of the patient support apparatus 20, 20a is turned on. In other embodiments, subsystem 54 is automatically activated based upon other events, such as the brake being turned on, an electrical cord being plugged into an electrical wall outlet, or another event. By always remaining on, or substantially always remaining on, measurement subsystem 54 is able to continuously monitor the weight sensed by load cells 36. The continuous weight readings taken by measurement subsystem 54 are stored in memory 58 and used for one or more of the purposes discussed in greater detail below. Memory 58 is any conventional electronic memory that is non-volatile, such as one or more EEPROMs, flash memory, or other suitable memory.

By having measurement subsystem 54 remain always on, or substantially always on, it is highly likely that weight readings will be taken by controller 56 prior to a patient entering the patient support apparatus 20, 20a. Measurement subsystem 54 therefore captures the weight detected by load cells 36 both prior to a patient entering patient support surface 28 and after the patient is positioned thereon. By capturing both of these weights, measurement subsystem 54 is able to determine the weight of the patient by subtracting the weight (if any) sensed by load cells 36 prior to the patient entering onto the support surface 28 from the weight sensed by load cells 36 after the patient has entered the support surface 28. This difference is equal to the patient's weight. Further, because the weight sensed by load cells 36 prior to the patient entering onto support surface 28 is known, the caregiver does not need to zero measurement system 54 prior to the patient entering onto patient support surface 28, as was required in many instances in the past.

In other words, in many past patient support apparatuses, if a patient entered onto the patient support surface prior to the caregiver zeroing the system, the subsequent weight reading would include whatever weight the patient was exerting on patient support surface, plus whatever weight was previously being exerted on the support surface (e.g. mattress, pillows, blankets). The weight reading would therefore be inaccurate with respect to the patient, and the patient would have to be removed to zero the system. Thereafter, the patient would re-enter the patient support surface and an accurate weight reading could be taken.

Measurement system 54 therefore eliminates the need for any manual zeroing of its weight measurement function. That is, one of the features that is able to be incorporated into measurement subsystem 54 is an auto-zeroing function for the scale system. By measuring the outputs of the load cells 36 nearly continuously, measurement subsystem 54 is able to determine a baseline weight sensed by load cells 36 prior to the patient entering, and then subtract this baseline weight from the weight measured after the patient enters the patient support apparatus 20, 20a, thereby avoiding the need to manually zero the weight scale system prior to the patient entering the bed. The extent the load cells were detecting weights prior to the patient entering the patient support apparatus 20, 20a, those readings are automatically eliminated from the patient's weight reading.

Figure 4:
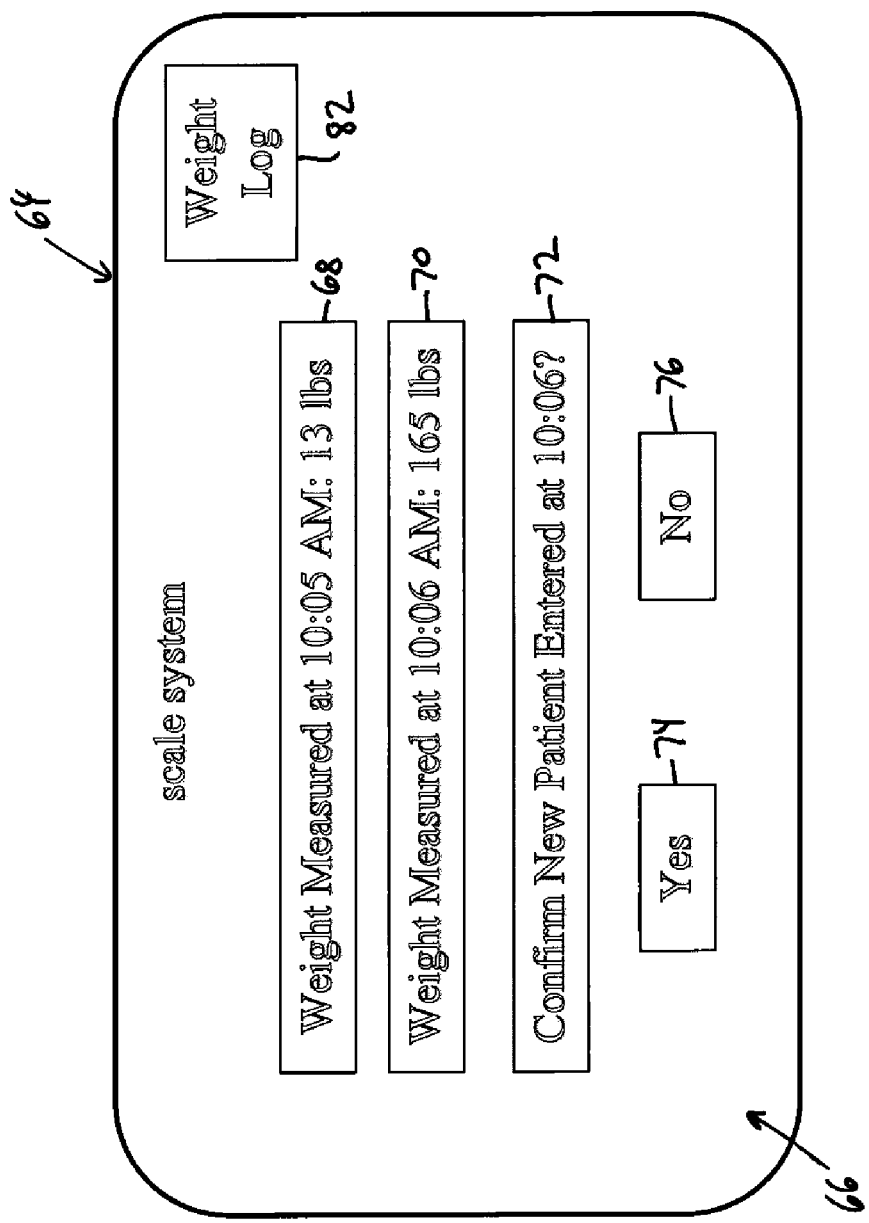
FIG. 4 is a view of an illustrative screen shot showing an auto-zeroing function of the measurement subsystem.

In at least one embodiment, measurement subsystem 54 communicates with display 64 on user interface 60 and shows the caregiver the weight readings both prior to and after the patient enters the patient support apparatus 20 or 20a. FIG. 4 shows an illustrative example of a screen shot 66 displayed on touchscreen display 64 that enables a caregiver to auto-zero a scale system contained with patient support apparatus 20 or 20a. Controller 56 is adapted to cause screen shot 66 to automatically appear after it detects what it concludes is the entry of a patient onto patient support apparatus 20, 20a. In other embodiments, controller 56 does not automatically display screen shot 66, but instead allows a caregiver to access screen shot 66 through appropriate manipulation of icons and/or menus on touchscreen display 64. Such icons may include, for example, an icon that brings up information regarding the scale system on patient support apparatus 20, 20a, and the screen shot with scale system information includes a link, button, menu, or other feature that enables a caregiver to access screen shot 66.

Regardless of how it is accessed, screen shot 66 includes a baseline weight indication 68 (FIG. 4). Baseline weight indication 68 tells the caregiver what cumulative weight was measured by load cells 36 prior to a patient entering on the patient support surface 28 of patient support apparatus 20, 20a. The number indicated in FIG. 4 is thirteen pounds, but this has been done merely for illustration purposes. The actual baseline weight reading is determined by taking a suitable number of readings from load cells 36 during a period of relative stability and averaging them. Appropriate filtering of the outputs may be performed in order to ensure the outputs are representative of a stable reading. If the baseline reading changes by a constant amount prior to the patient entering patient support surface 28, then controller 56 will display the most recent baseline reading at baseline weight indication 68. Further, any such changes in the baseline weight reading will be logged, as will be described in greater detail below, and made available for review by the caregiver.

Screen shot 66 (FIG. 4) further includes a current total weight indication 70. Current total weight indication 70 displays the current total weight detected by load cells 36. This total weight is read from the load cells and calculated in any conventional manner, as would be known to one of ordinary skill in the art.

Screen shot 66 (FIG. 4) also includes a confirmation indicator 72 showing that controller 56 has determined that it is likely that a patient has entered patient support surface 28. Confirmation indicator 72 requests that the caregiver confirm that a patient has indeed entered onto patient support surface 28. Confirmation is provided or rejected by way of a yes button 74 or a no button 76. Yes and no buttons 74 and 76 are not physical buttons, but instead are images displayed on touchscreen display 64 that, when pressed cause controller 56—or a controller inside of user interface 60—to react appropriately. In some alternative embodiments, measurement subsystem 54 is configured to automatically recognize that a patient has entered onto patient support surface 28 without asking for confirmation from the caregiver. Regardless of whether confirmation is needed or not, controller 56 determines, in one embodiment, that a patient has likely entered onto patient support surface 28 when a weight increase above a predefined threshold takes place. Such threshold may vary, but in one embodiment is one hundred pounds. In other embodiments, as will be discussed in greater detail below, controller 56 determines that a patient has likely entered onto patient support surface 28 by also, or alternatively, consulting signals from one or more vital sign sensors that are adapted to detect one or more vital signs of a patient positioned on patient support surface 28.

Figure 5:
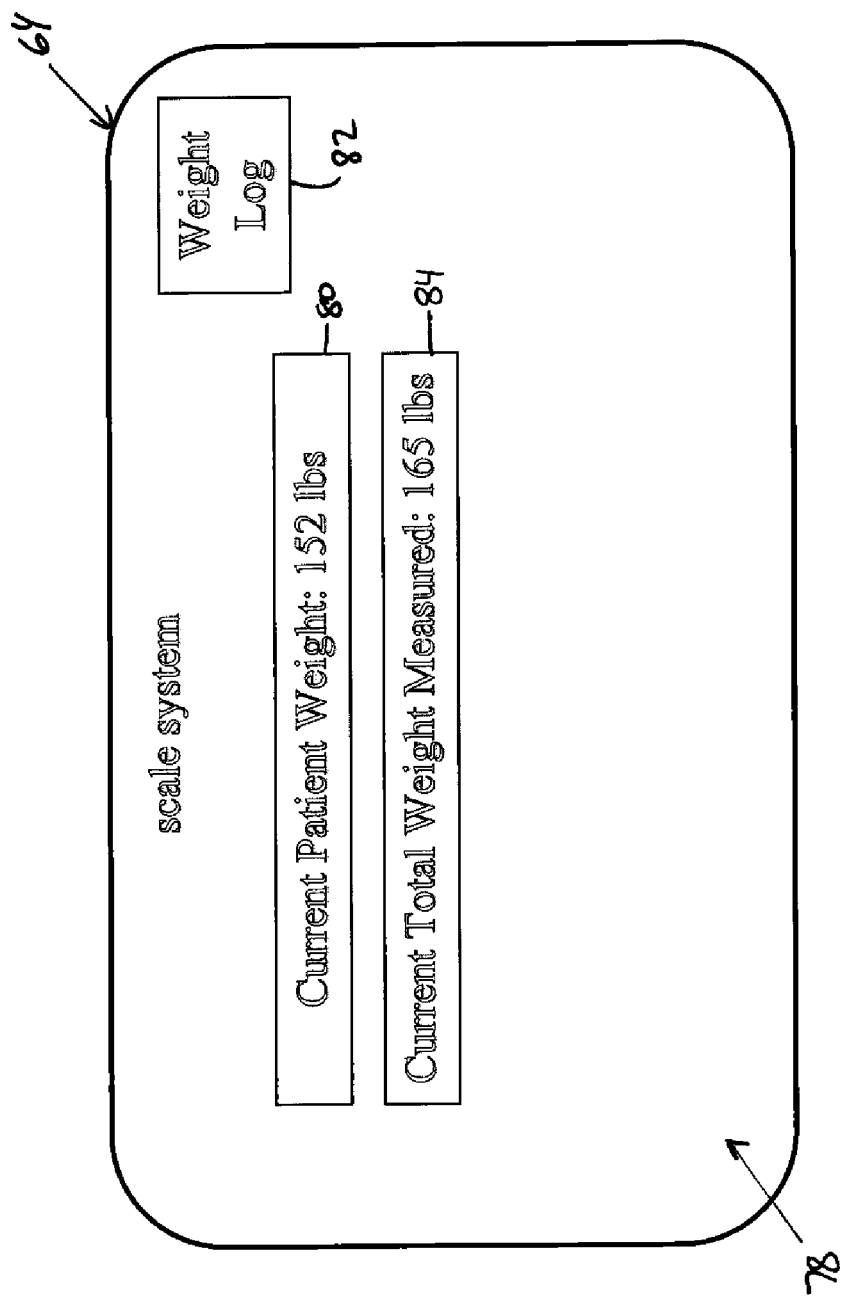
FIG. 5 is a view of another illustrative screen shot showing a weight display function of the measurement subsystem.

If a caregiver presses the yes button 74 (FIG. 4) and confirms that a patient has indeed entered patient support surface 28, then a new screenshot 78 is displayed, one illustrative example of which is shown in FIG. 5. Screenshot 78 includes a total patient weight indicator 80 that displays the currently measured weight of the patient. In this example, the currently measured patient weight is 152 pounds, although it will be understood that this is merely an illustrative example. This patient weight is computed by subtracting the baseline weight displayed in indicator 68 (13 pounds in FIG. 4) from the total weight displayed in indicator 70 (165 pounds in FIG. 4). By confirming that a patient entered onto patient support surface 28 immediately following the baseline weight reading shown at indicator 68, controller 56 knows that the weight increase that took place at approximately 10:06 AM was due to a patient, and is therefore able to attribute this weight change to the patient. Because the baseline weight was known immediately previously to this change, it is not necessary for the caregiver to zero the system to determine this patient weight because this zeroing effectively happens automatically through the subtraction of the weight reading displayed at indicator 68 from the weight reading displayed at indicator 70.

Figure 7:
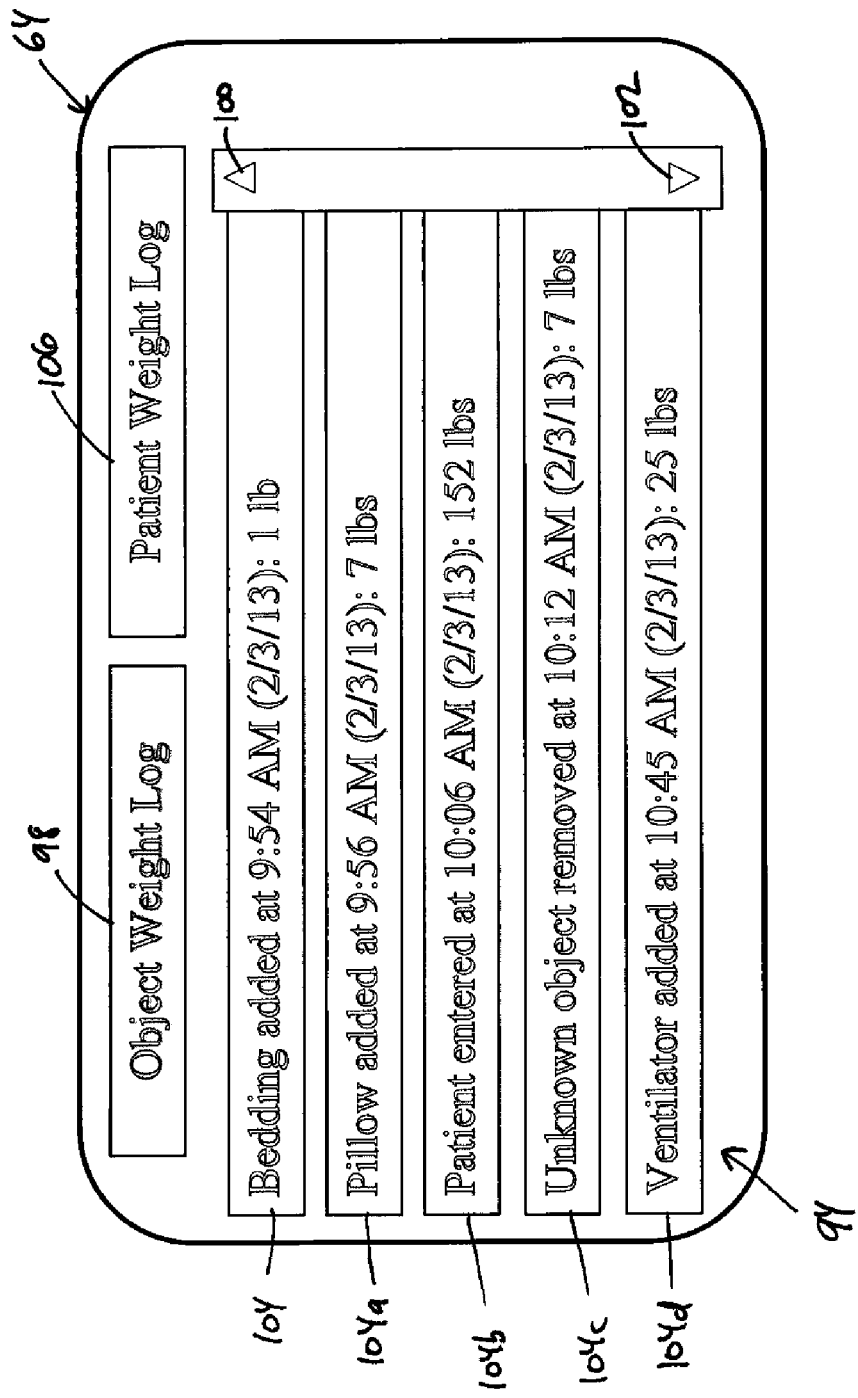
FIG. 7 is a view of another illustrative screen shot showing one portion of a weight log maintained by the measurement subsystem.

Screen shot 78 further includes an indicator 84 that displays the current total weight measured by load cells 36. In this illustrated example, the current total weight matches that measured at 10:06 AM (as shown in indicator 70 in FIG. 4) because no other objects have been added or removed from the patient support surface 28 since the patient entered it. However, if objects are added to, or subtracted from, the patient support surface 28 after the patient has entered (e.g. after 10:06 AM in this example), the weight displayed at indicator 84 will change. As will be explained in greater detail below, a caregiver is able to obtain additional information about these subsequent weight changes by pressing on a weight log icon 82 that will bring up a weight log screenshot 94, one example of which is shown in FIG. 7, which includes an explanation for this weight change.

Figure 6:
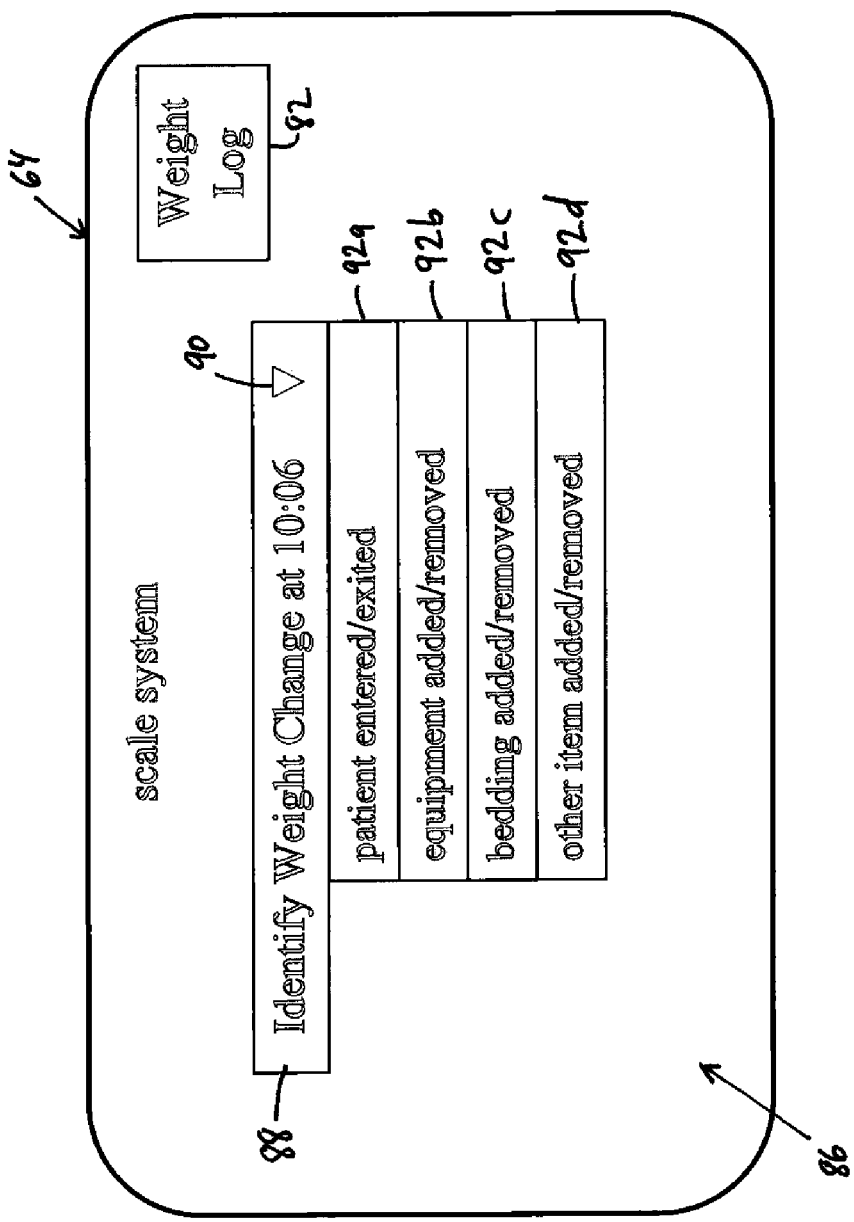
FIG. 6 is a view of another illustrative screen shot showing a weight event identification function of the measurement subsystem.

If a caregiver rejects the patient entry indication of indicator 72 (FIG. 4) by pressing on no button 76, then display 64 will display a different screen shot, such as a screen shot 86 shown in FIG. 6. Screen shot 86 displays an identify indicator 88 that enables a caregiver to identify what caused the weight change indicated on screen shot 66 (i.e. the weight change at 10:06 AM in this example). Identify indicator 88 includes a menu icon 90 that, as displayed, is a downward arrow. Pressing on menu icon 90 generates a number of potential identity indicators 92*a*, 92*b*, 92*c*, 92*d*, etc. that are displayed underneath identity indicator 88. Potential identity indicators 92 list possible identifications of the cause for the weight change detected at 10:06 AM (in this example). As shown, potential identity indicator 92*a* corresponds to a patient having entered or exited patient support surface 28; potential identity indicator 92*b* corresponds to a piece of equipment having been added or removed from patient support surface 28; potential identity indicator 92*c* corresponds to bedding being added or removed from patient support surface 28; and potential identity indicator 92*d* corresponds to an unidentified object being removed or added to patient support surface 28. Once a caregiver presses on the appropriate identity indicator 92, controller 56 will store that identity in memory, including the weight change corresponding to that identity, as well as the time when that weight change occurred. In other words, the selection made by the caregiver from the various identity indicators 92 will be stored in a weight log that, as discussed in more detail below, is accessible by pressing on weight log icon 82.

The list of potential identity indicators 92 shown in the screen shot 86 of FIG. 6 is not intended to be a complete list. Additional potential identities can be added. As but one example, a potential identity indicator 92 corresponding to the addition or removal of pillows could be added. Still other potential identity indicators 92 are possible.

The "other item" potential object identity indicator 92*d* shown in FIG. 6 enables a caregiver to custom identify an object whose identity does not appear in the list of potential identity indicators 92 displayed on screen shot 86. When a caregiver presses on indicator 92*d* in FIG. 6, a screen shot (not shown) is displayed that includes a full QWERTY keyboard and a space for typing a custom identity of the object that was added or removed (in this example, the object added at 10:06 AM). After the caregiver types the appropriate identification, he or she presses an enter or return icon that records the typed identification in the weight log. If the caregiver does not know the identity of the object added or removed, the caregiver can type in "unknown," or decline to type anything, in which case the object will be automatically identified by measurement system 54 as "unknown" in the weight log.

In some embodiments, greater granularity is provided to a caregiver after selecting one of the potential identity indicators 92. That is, after the caregiver presses one of these buttons, another menu of items that are described with greater specificity is provided, and the caregiver is able to select a more specific object corresponding to the weight change. For example, if the caregiver presses on the equipment added/removed indicator 92*b*, a subsequent menu is displayed that identifies various specific types of equipment. Such equipment includes, for example, pumps, ventilators, respirators, IV poles, etc. Once the caregiver selects the specific types of equipment (or enters a default equipment identity if the correct one is not listed), measurement subsystem 54 records the identity in the weight log.

FIG. 7 shows an illustrative weight log screen shot 94 that is displayable on touch screen display 64 in response to a caregiver pressing the weight log icon 82, which appears in screen shot 66 (FIG. 4), screen shot 78 (FIG. 5), and screen shot 86 (FIG. 6). Access to weight log screen shot 94 may also be provided in different manners (such as a button or icon on a main menu for touch screen display 64). Weight log screen shot 94 provides two different types of weight changes—those associated with patient weight changes and those associated with object removals or additions. It will be understood by those skilled in the art that, in other embodiments, the weight changes for the patient's weight could be combined into a single log with the object weight changes. In the example shown in FIG. 7, the object weight log has been chosen for display, as indicated by a darkened object weight log indicator 98.

Weight log screen shot 94 (FIG. 7) displays a log of weight changes, including when the weight changes occurred, the magnitude of the weight change, and a magnitude of the weight change. As shown, these elements are displayed in chronological order, with older weight changes appearing at the top and more recent weight changes appearing at the bottom. An up arrow icon 100 and a down arrow icon 102 change the time range for the displayed set of logged weight changes when pressed. In other words, pressing on up arrow icon 100 in the example of FIG. 7 will display weight log events that occurred prior to 9:54 AM, while pressing on down arrow icon 102 will display weight log events that occurred after 10:45 AM (if any). The speed at which the time range changes may accelerate if the caregiver presses and holds down on either of up or down arrow icons 100 or 102. Further, other icons or inputs can be included on screen shot 94 that enable the caregiver to enter a custom time range.

The weight events included in the weight log are initially generated automatically by controller 56 based on one or more algorithms that will be described in greater detail below. However, the caregiver is provided the opportunity to confirm or reject each and every one of the automatically generated identifications. Such rejection and confirmation can be carried out in a variety of different manners. One manner is illustrated in FIG. 4 and described above for confirming or rejecting the entry of a patient onto patient support surface 28. Another method includes touching any of weight event indicators 104 shown in FIG. 7. Touching weight event indicator 104 will bring up another screen shot (not shown) in which the caregiver is given the opportunity to confirm or reject the identification of the object proposed by controller 56. If the caregiver rejects the proposed identification, he or she is given the opportunity to input a custom identification of the weight event. Whatever custom identification he or she inputs will then be displayed as a weight event 104 on screen shot 94. If he or she chooses not to enter any identification, the weight event 104 will be listed as "unknown."

If a caregiver accepts a proposed identification of a weight event 104, the identification is recorded by controller 56 and stored in memory. Further, in some embodiments, controller 56 is configured to change an aspect of the confirmed weight event indicators 104 so that they are differentiated from those weight event indicators 104 that have not been confirmed by the caregiver. This differentiation may be made in any suitable manner, such as by changing the background colors of the confirmed weight event indicators 104 to a color different from the unconfirmed weight event indicators, changing the border line color or thickness for the event indicators 104, adding or changing a symbol positioned in or adjacent to each of the event indicators, or by other means. Whatever method is utilized, the caregiver is presented with a log of weight events 104 on screen 94 wherein those weight events 104 that have been confirmed are clearly and easily distinguishable from those weight events 104 that have not been confirmed.

To the extent desired, the caregiver can then confirm any unconfirmed weight events 104, or otherwise alter them so that they are correct. The weight log entries shown in FIG. 7 are stored in memory 58 on board the patient support apparatus 20, 20a and retained until a caregiver manually erases them. In some embodiments, as will be discussed in greater detail below, the weight event log entries are forwarded to one or more healthcare network applications or servers running on a healthcare network. Such applications or servers may include, among others, an electronic medical record system.

As was noted, the screen shot 94 shown in FIG. 7 illustrates the weight events 104 that are associated with object entry and exit (as well as patient exit and entry). Measurement subsystem 54 also keeps track of changes in patient weight. In order for a caregiver to access these, he or she presses on the patient weight log indicator 106 shown in FIG. 7. Such pressing will bring up another screen shot on display 64, such as the screen shot 108 shown in FIG. 8. Screen shot 108 is associated with patient weight change events, as indicated by the darkened background of patient weight log indicator 106. Pressing on object weight log 98 on screen shot 108 will return the caregiver to screen shot 94 of FIG. 7.

Patient weight log indicator 106 (FIG. 8) includes a listing or log of patient weight events 110. These patient weight events 110 are displayed in chronological order in a fashion similar to the object weight event indicators 104 of FIG. 7. Further, the patient weight events 110 are displayed over a time range that is adjustable through the use of up and down arrow icons 100 and 102, in the same manner as has been discussed above with respect to FIG. 7. The patient weight events 110 listed on screen shot 108 include the time and measured weight of the patient whenever he or she enters patient support surface 28, as well as whenever he or she leaves patient support surface 28. Further, the patient weight events 110 listed on screen shot 108 include the amount of weight gained or lost by the patient while residing on the patient support surface 28, including the beginning time and ending time of the measured weight change. Patient weight event indicators 110a and 110c in FIG. 8 show examples of this type of patient weight change event, including the time interval over which these changes occurred.

Figure 8:
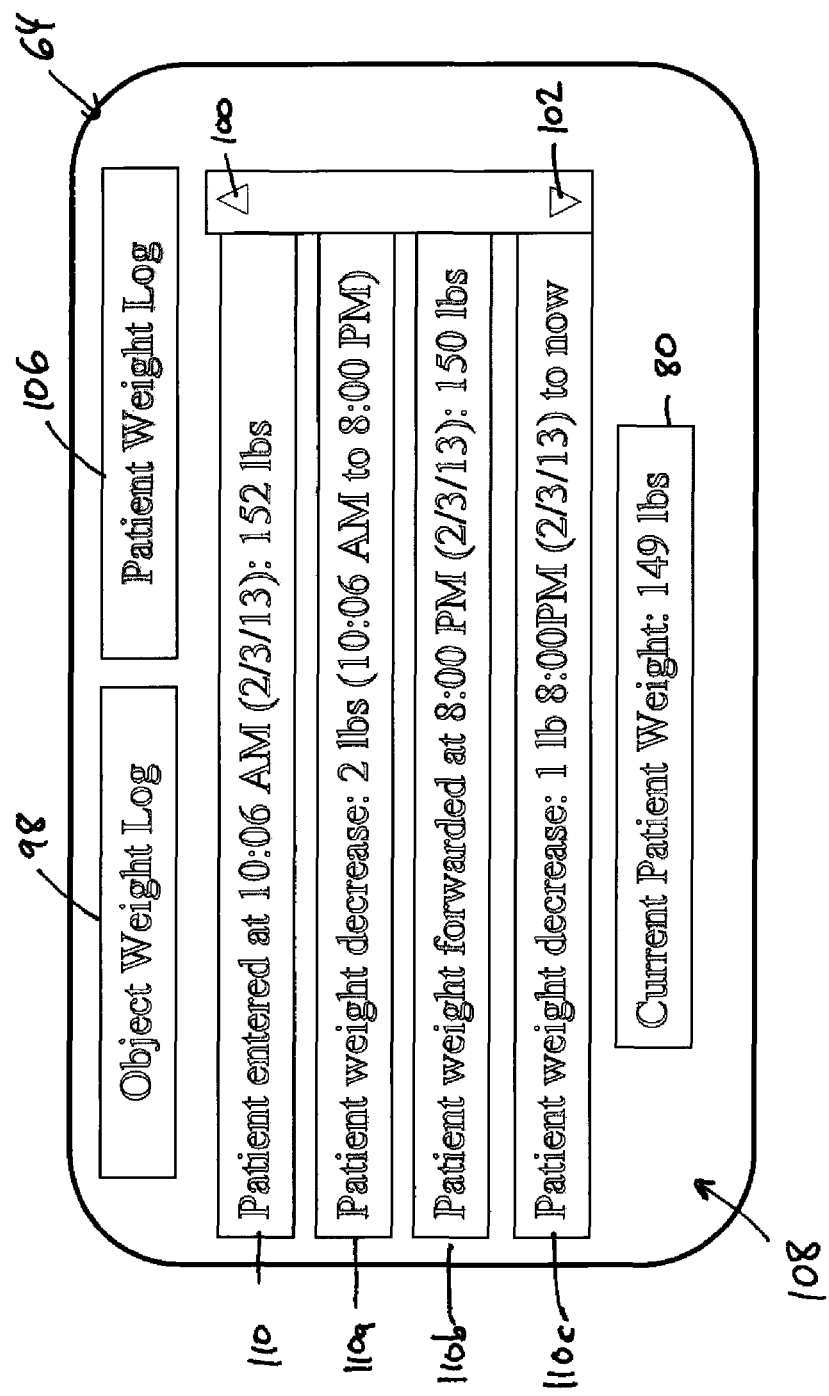
FIG. 8 is view of another illustrative screen shot showing a second portion of the weight log maintained by the measurement subsystem.

In the embodiment shown in FIG. 8, screen shot 108 also lists patient weight events 110 corresponding to weight measurements that have been forwarded by a caregiver to a location remote from the patient support apparatus 20, 20a, such as an electronic medical record system. An example of this is shown by weight event 110b where the caregiver forwarded the patient weight reading taken at 8:00 PM to the patient's electronic medical record. This forwarding is carried out in any suitable manner, such as by transmitting it through a WiFi connection on the bed to a healthcare network having an electronic medical records system server or application.

Still further, although not shown on the illustrative screen shot 108 of FIG. 8, measurement subsystem 54 also records and lists as a patient weight event 110 any auto-zeroing function carried out by a caregiver. Such auto-zeroing can take place shortly after a patient enters the patient support surface 28 (as was described above with respect to FIGS. 4 and 5), or it may take place at any time that a caregiver chooses, regardless of how long the patient may or may not have been lying on the patient support surface 28. By pressing an appropriate button 62 on user interface 60, or touching an appropriate icon on touch screen display 64, measurement subsystem 54 allows a caregiver to manually zero the weight readings sensed by load cells 36 at any time. If a patient is already positioned on patient support surface 28, controller 56 will capture the current weight reading and subtract from it the last baseline weight reading corresponding to when the patient first entered the patient support surface. This baseline reading is computed by subtracting from the currently captured weight reading all recorded non-patient weight increases that have occurred since the time the patient first entered the patient support surface 28, and adding to the currently captured weight reading all recorded non-patient weight decreases (e.g. to account for objects that may have been removed). Recorded weight changes that correspond to changes in the patient weight (e.g. patient weight gain or weight loss entries 104) are neither subtracted nor added to the currently captured weight reading.

Therefore, for example, if the patient had entered five hours previously, and during those five hours a one pound pillow had been removed and a thirty-five pound piece of medical equipment had been set on the patient support surface 28 (or other a portion of the patient support apparatus 20, 20a that influenced the load cells 36), controller 56 would add one pound to the current total weight reading and subtract thirty-five pounds from the currently captured total weight reading, for a net change of negative 34 pounds. Therefore, if the current total weight reading was 180 pounds, controller 56 would calculate that the current weight of the patient is 146 pounds (180+1−35=146). Any changes in the patient weight that had been detected in the five hours since the patient entered onto patient support surface 28, which would be recorded as patient weight event indicators 104, would not be used in this auto-zeroing calculation.

Figure 9:
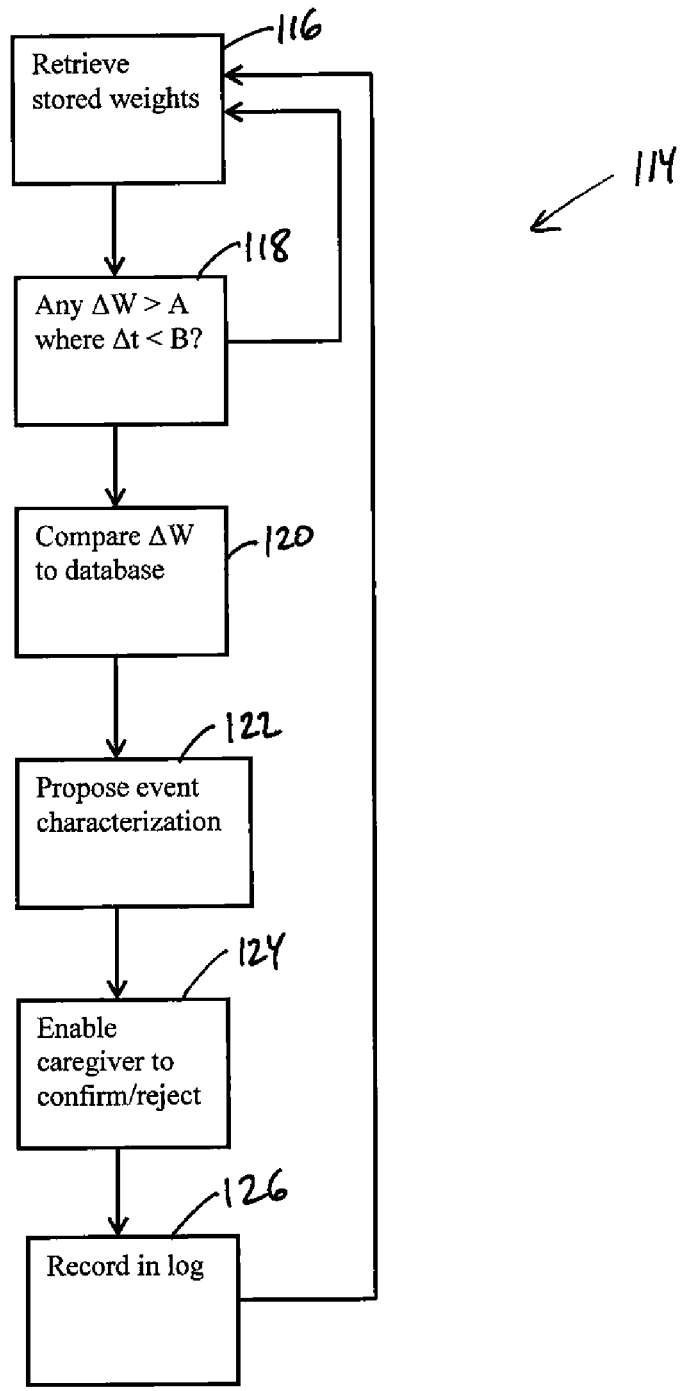
FIG. 9 is a flowchart of a weight event identification algorithm that is used by the measurement subsystem.

FIG. 9 illustrates an event identification algorithm 114 that is used by controller 56 in proposing the identification or characterization of events in the patient and object weight logs. Algorithm 114 begins at a retrieval step 116 where weight readings taken by load cells 36 are retrieved from memory 58. Such weight readings, as was noted previously, are taken nearly continuously from the moment power is supplied to patient support apparatus 20 or 20a, or another initiation event occurs. These weight readings are taken multiple times per second and recorded in memory 58. Algorithm 114 finds and characterizes events of significance in these recorded weights by first retrieving them at step 116, and then examining them at step 118. More specifically, during step 118, controller 56 examines the retrieved weight readings to determine if the weight readings represent a change in weight greater than a weight threshold (exemplified as threshold A in FIG. 9) that occurs during a time period less than a time threshold (exemplified as threshold B in FIG. 9). In other words, controller 56 examines the weight retrieved at step 118 to see if there are any significant weight changes (greater than the weight threshold) that occur within a relatively short time period (less than time threshold B). If the weight changes are less than the threshold, then controller 56 interprets these changes as being due to the patient's weight slowly changing. Such miniscule changes are not individually noted as a patient weight event 110, but instead are recorded, cumulatively summed, and entered into the patient weight log as an event 110 when another event occurs, such as the patient entering or leaving the patient support surface 28, or an object being added or removed from patient support surface 28. While the precise value of the weight threshold may vary, in one embodiment, it is on the order of a fraction of a pound.

Controller 56 also examines at step 118 the time period over which a weight change occurs. If the weight change occurs gradually, then controller 56 interprets this as the patient's weight changing. If the weight change occurs suddenly, then controller 56 interprets this as an object or person entering or exiting the patient support surface 28. While the precise time may vary, in one embodiment the time threshold is on the order of a couple of seconds.

If no weight changes are detected at step 118 that meet both the time and weight change thresholds (A and B in FIG. 9), the controller returns to step 116 and retrieves any stored weights that have not yet been analyzed by algorithm 114. If a weight change is detected at step 118 that meets both the time and weight change thresholds, the controller moves to step 120 where it compares the weight change to a database. The database contains a listing of weight change ranges that are mapped to potential objects or reasons for the weight change. For example, the database may characterize any weight changes of greater than 100 pounds as likely corresponding to a patient entering or exiting the patient support surface 28. Other thresholds for characterizing the weight change as a person exiting or entering can, of course, be used (particularly if the patient support apparatus is used in a pediatric setting). The database might also characterize any weight changes of less than 5 pounds but greater than the weigh threshold A (step 118 of FIG. 9) as likely corresponding to a change in bedding or a pillow being added or removed. Changes in weight greater than this threshold, but less than the threshold corresponding to a patient entering or exiting, could be assigned as corresponding to medical equipment being removed or added. To give algorithm 114 greater accuracy, the weights of medical devices, bedding, and/or other objects that are commonly used in conjunction with the patient support apparatus 20 can be input into the database along with their identity (all of which is stored in memory 58).

At step 122, controller 56 characterizes the weight change based upon the information located in the database at step 120. That is, controller 56 searches through the database and finds the weight entry stored therein that is the closest match for the weight change identified at step 118. If there are no close matches, then controller 56 characterizes the weight change at step 122 as "unknown," or some other equivalent characterization. If controller 56 finds a match in the database, it characterizes the weight change according to what is identified in the database. Examples of such weight characterizations are shown in FIGS. 6 and 7 and illustrated in potential identity indicators 92 and weight event indicators 104. In other words, controller 56 will characterize weight events at step 122 in such manner as: pillow added/removed; or bedding added/removed; or ventilator added/removed; or medical device added/removed; or patient exited/entered; or unknown object added/removed; or the like.

After making a preliminary or proposed identification of the weight events detected by controller 56, controller 56 enables the caregiver to confirm or reject these preliminary or proposed identifications at step 124 of algorithm 114. If the caregiver neither confirms nor rejects these proposed identifications, they are recorded at step 126 as unconfirmed. If the caregiver accepts the proposed identifications, they are recorded at step 126 as confirmed. If the caregiver rejects the proposed identification, the caregiver is given the opportunity to manually identify the weight event, which then is recorded at step 124 as confirmed. If the caregiver does not manually identify the rejected weight event, it is recorded as an unknown weight event at step 126.

The records recorded into the log at step 126 are made available for viewing by the caregiver via touch screen display 64. FIGS. 7 and 8 illustrate arbitrary examples of the display of these records. Further, as was noted above, the illustrative screen shots of FIGS. 7 and 8 allow, in at least some embodiments, a caregiver to confirm or reject the proposed characterization simply by pressing on the item 104, which will bring up a different screen (not shown) that enables a caregiver to identify the object.

Figure 10:
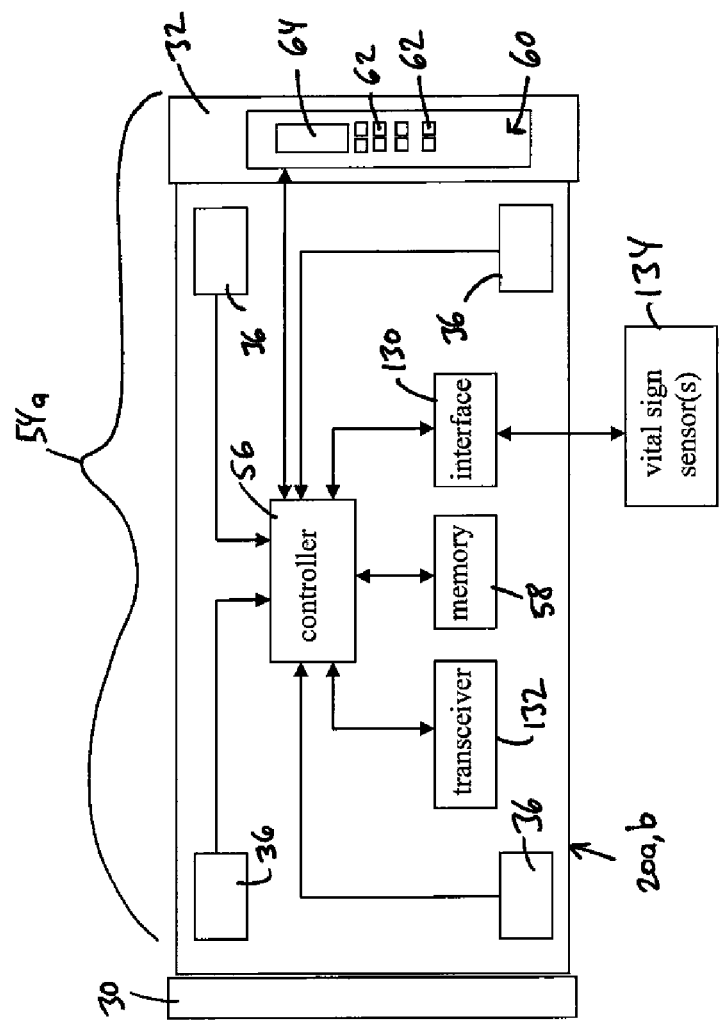
FIG. 10 is a plan view diagram of a second measurement subsystem that may be incorporated into either of the patient support apparatuses of FIG. 1 or 2.

FIG. 10 illustrates an alternative embodiment of a measurement subsystem 54a. Measurements subsystem 54a is capable of being incorporated into either or both of patient support apparatuses 20 and 20a. Those components of measurement subsystem 54a that are the same as corresponding components of measurement subsystem 54 are identified by the same reference number, while those components of measurement subsystem 54a that are not in subsystem 54 are identified by new reference numbers.

The physical architecture of measurement subsystem 54a differs from subsystem 54 in that it includes an interface 130 and a transceiver 132, both of which are in electrical communication with controller 56. Interface 130 is adapted to communicate with one or more vital sign sensors 134 so that controller 56 may use these vital sign signals (or absence of them) for improving the characterization of weight events, and/or for other purposes, as will be described herein. Interface 130 is a USB (Universal Serial Bus) port in one embodiment, although it will be understood by those skilled in the art that it may take on a variety of different forms, such as, but not limited to, an RS-232 port, a wireless interface, or any other suitable port for communicating information with vital sign sensor 134.

Transceiver 132 is used by controller 56 for forwarding selected information from measurement subsystem 54a to other devices, such as a hospital Ethernet, or another recipient. In one embodiment, transceiver 132 is a WiFi radio capable of communicating with a wireless access point of the hospital Ethernet in accordance with IEEE 802.11 standards, or in accordance with other standards. More specific uses of transceiver 132 are discussed below.

The vital sign sensor 134 may be any conventional sensor used to measure one or more patient vital signs, such as, but not limited to, respiration rate and heart rate. While other types of sensors can be used, non-invasive vital sign sensors 134 have advantages over invasive sensors 134 in that the vital signs can be measured without having to attach anything to the patient. In one embodiment, vital sign sensor 134 is a pressure sensing mat that is positioned on top of, or integrated into, a mattress (not shown) positioned on top of patient support surface 28. Such a pressure sensing mat includes an array of pressure sensors adapted to detect interface pressure exerted by a patient on the mattress. By analyzing those pressure sensors positioned in the vicinity of the patient's thoracic cavity, respiration and/or heart rate signals can be determined. In one embodiment, vital signs sensor 134 is a pressure sensing flexible mat like that disclosed in commonly assigned PCT patent application serial number PCT/US12/27402 filed Mar. 2, 2012 by Stryker Corporation, and entitled SENSING SYSTEM FOR PATIENT SUPPORTS, the complete disclosure of which is hereby incorporated herein by reference. In such an embodiment, the pressure sensing flexible mat outputs both a patient respiration rate and a patient heart rate.

In another embodiment, vital signs sensor 134 is a vital sign sensor incorporated into a mattress, such as the mattress disclosed in commonly assigned U.S. patent application Ser. Nos. 13/836,813 and 61/697,010, entitled INFLATABLE MATTRESS AND CONTROL METHODS and PATIENT SUPPORT, respectively, the former of which was filed Mar. 15, 2013 and the latter of which was filed Sep. 5, 2012, the complete disclosures of both of which are hereby incorporated herein by reference. When incorporated into a mattress, the vital sign sensor, in some embodiments, detects respiration and/or heart rates by a pressure sensor included within the mattress that detects fluid pressure changes within one or more bladders contained within the mattress. Such fluid pressure changes are filtered for frequencies within those of the normal heart rate and breathing rate and processed, such as through Fourier analysis, or otherwise, to yield a heart rate and/or respiration rate. In embodiments using the mattress construction disclosed in the above-referenced Ser. No. 13/836,813 and/or 61/697,010 applications, the mattress also includes a plurality of depth sensors that measure the depth which the patient has sunk into the mattress. These depth sensor signals may be combined with the air pressure signals to determine a patient's breathing rate and or heart rate.

In still another embodiment, vital signs sensor 134 is incorporated into the patient support apparatus 20 or 20a itself. For example, in one embodiment, the vital signs sensor uses the load cells 36 to detect vibrations caused by the patient's breathing and/or heart beating. These signals are processed—such as by controller 56 or another suitable controller—to determine a patient's heart rate and/or breathing rate. A more detailed description of how the load cells 36 can be used to determine a patient's breathing rate and/or heart rate is disclosed in commonly assigned U.S. Pat. No. 7,699,784 issued to Wan Fong et al. and entitled SYSTEM FOR DETECTING AND MONITORING VITAL SIGNS, the complete disclosure of which is hereby incorporated herein by reference.

Figure 11:
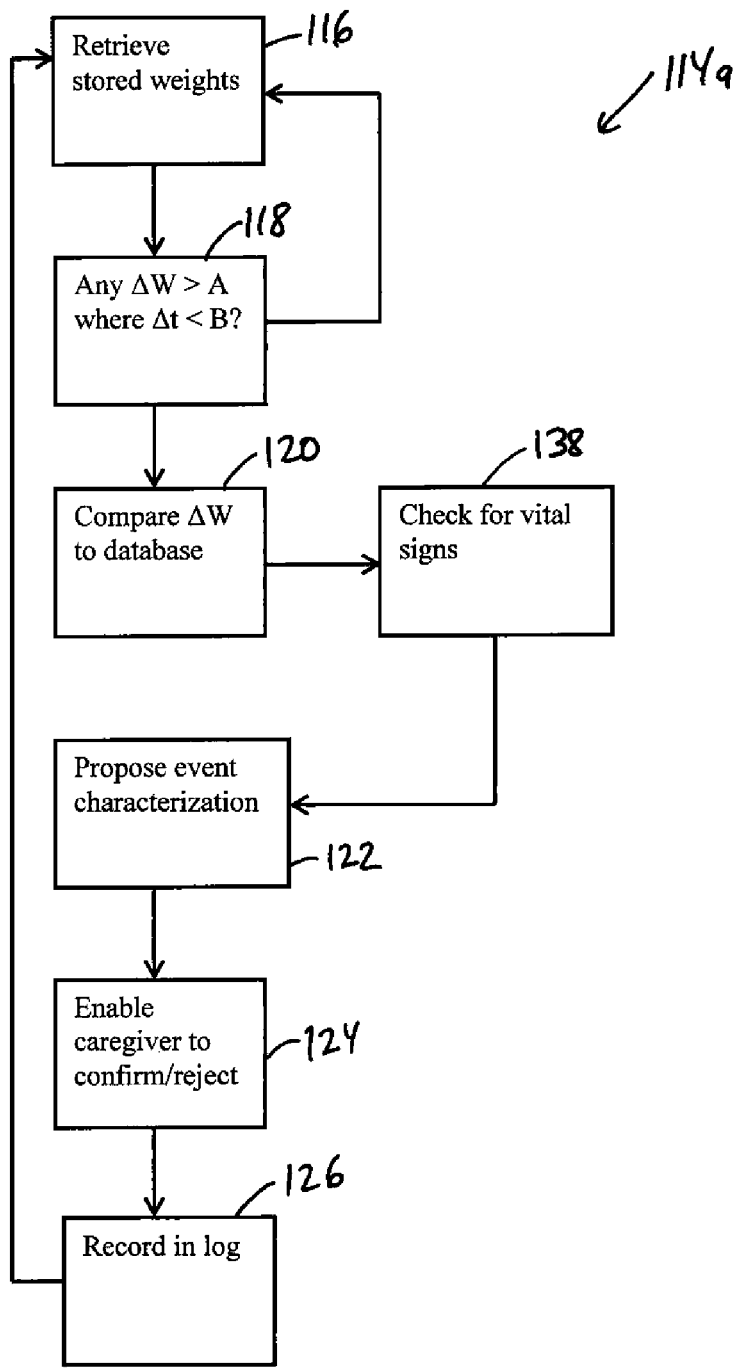
FIG. 11 is a flowchart of a second weight event identification algorithm that may be used by the measurement subsystems of FIG. 10 or 15.

Regardless of the physical form of the vital sign sensors 134, controller 56 is adapted, in at least one embodiment, to use these vital sign signals to distinguish between non-human objects on patient support surface and humans positioned thereon. Knowing this difference is useful in at least several different situations. For example, the vital sign information can be used for better identifying the weight events listed in any of the weight logs discussed herein. More particularly, FIG. 11 illustrates an alternative event identification algorithm 114a that uses the vital sign information from sensors 134 to facilitate the identification of the objects that are added to, or removed from, patient support surface 28. The steps of algorithm 114a that are the same as those of algorithm 114 are labeled with the same reference numbers and carry out the same functions that have been previously been described above with respect to algorithm 114. The difference between algorithms 114a and 114 is the addition of a vital signs check step 138.

Vital signs check step (FIG. 11) follows step 120 where controller 56 has consulted a database of weight changes and potential objects/persons that might correspond to the detected changes. Controller 56 uses the presence or absence of vital sign signals at step 138 to better select the proper characterization from the event database. That is, if no vital signs are detected at step 138, then controller 56 will not characterize a weight increase as a patient entering the patient support apparatus, even if the weight increase is otherwise above the threshold corresponding to a potential human entering the patient support apparatus (e.g. 100 pounds, in some embodiments). Still further, controller 56 records the absence or presence of vital signs signals from sensor 134 and uses the history of these signals near the time of the weight event to help characterize the event. For example, if the load cells detect the removal of, say, 90 pounds of weight, controller 56 will check to see if vital signs were detected immediately before this 90 pound weight removal, and if vital signs are currently being detected (after the removal). If vital signs were previously detected, but are not currently detected, controller 56 interprets this removal of 90 pounds as a patient exit. However, if vital signs were previously detected and are still detected, then controller 56 concludes that the patient is still on the patient support surface, and characterizes this weight loss as an object removal, not a person removal. In still other situations, if no vital signs were detected both before and after the weight decrease, controller 56 will characterize the weight removal as an object removal.

Vital signs sensor 134 therefore provides additional information to controller 56 that enables it to better characterize the weight change events detected by load cells 36. In particular, vital signs sensor 124 allows controller 56 to better distinguish between the movement of inanimate objects and living beings onto and off the patient support surface. After checking for the absence or presence of vital signs at step 138, controller 56 proceeds to step 122 and proposes a characterization of the weight event, in the same manner that has been previously discussed. The rest of algorithm 114a operates in the same manner as algorithm 114.

Figure 12:
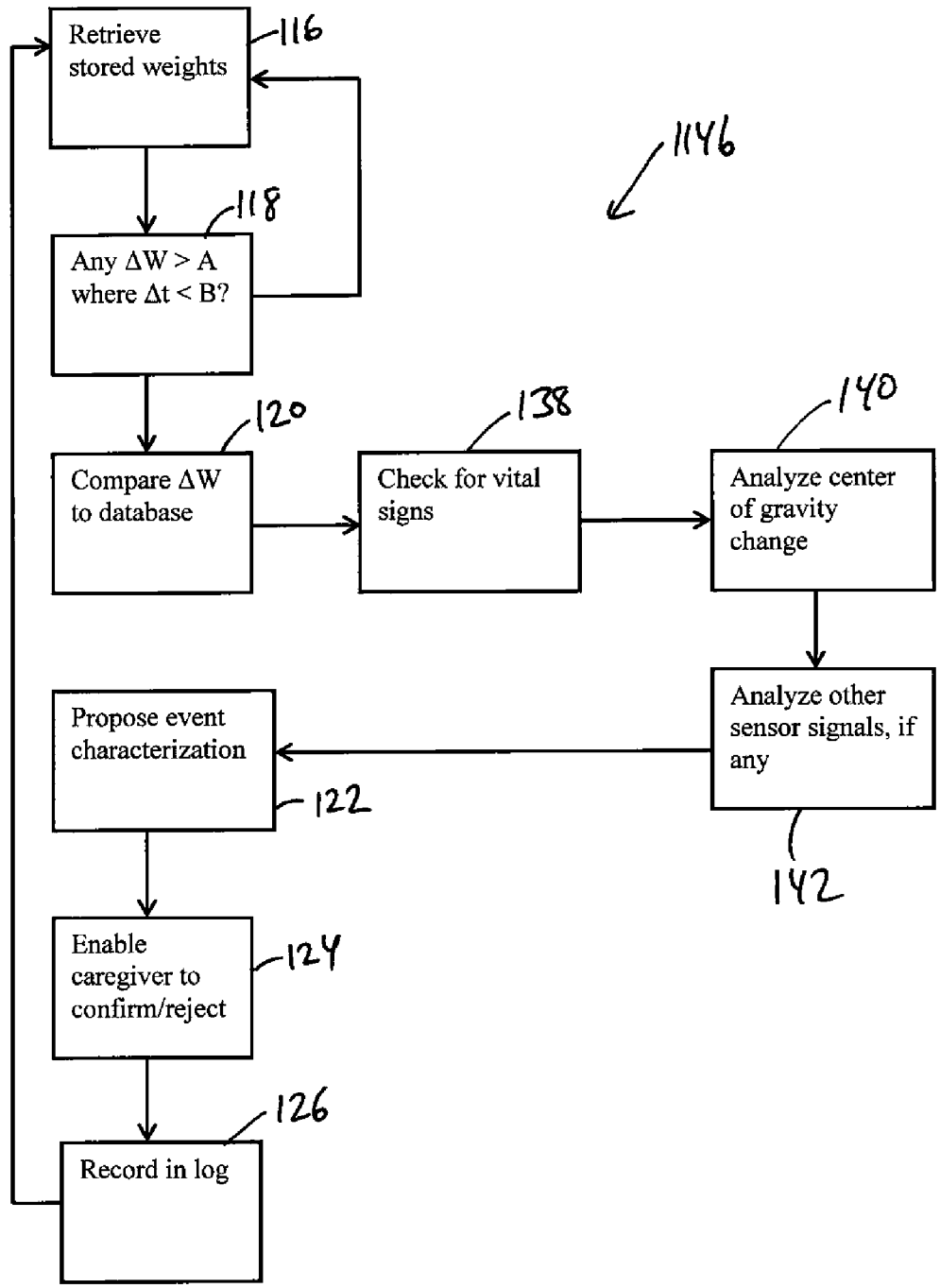
FIG. 12 is a flowchart of a third weight event identification algorithm that may be used by the measurement subsystems of FIG. 10 or 15.

FIG. 12 illustrates another alternative embodiment of an event identification algorithm 114b. As with algorithms 114 and 114a, algorithm 114b is carried out by controller 56, and may be implemented on any of the patient support apparatuses described herein (e.g. 20 or 20a). Algorithm 114b differs from algorithm 114a by the addition of two additional steps: a center of gravity analysis step 140 and an additional sensor analysis step 142 (if any additional sensors are present). During center of gravity analysis step 140, controller 56 compares the calculated center of gravity of the mass on patient support surface immediately prior to the weight event to the calculated center of gravity immediately after the weight event. These calculations of the center of gravity are performed using known techniques, such as those disclosed in commonly assigned U.S. Pat. No. 5,276,432 issued to Travis and entitled PATIENT EXIT DETECTION MECHANISM FOR HOSPITAL BED, the complete disclosure of which is hereby incorporated herein by reference.

During the comparison of the calculated centers of gravity immediately prior to and immediately after the weight event at step 140, controller 56 determines which direction the center of gravity has moved, and the magnitude of the change in the center of gravity. This direction and magnitude are used by controller 56 in its proposed identification of the objects added to, or removed from, patient support surface 28. For example, if the center of gravity shifts toward the head end of patient support apparatus 20 in a manner that is generally consistent with the usual placement of a pillow, controller 56 will use this information to identify the object added or removed as a pillow (assuming the weight change is within the expected weight range for pillows). As another example, if bedding is removed or added, the center of gravity of such bedding is very close to the center of the patient support surface 28 (because the bedding is normally spread out over the entire support surface, or nearly the entire support surface), and little, if any, change in the center of gravity will be detected. Controller 56 uses this information in identifying, or ruling out, the addition or removal of bedding as corresponding to the weight event. In still other situations, the use of medical equipment added to, or removed from, the patient support apparatus may normally be expected to occur at certain positions on the patient support surface, which will change the center of gravity in predictable manners. These expected changes in centers of gravity are stored in memory 58 and used for more accurate identification of the weight events detected by the load cells 36.

After completing step 140, controller 56 moves onto step 142 in algorithm 114b (FIG. 12). At step 142, controller 56 analyzes any additional sensor information in order to be able to more accurately characterize the weight event at step 122. Such additional sensor information may include any suitable sensors. In one embodiment, the additional sensors include a flexible pressure sensing array positioned on top of, or incorporated into, the mattress supported on the patient support apparatus. One example of such a flexible pressure sensing array is disclosed in the above-mentioned commonly-assigned PCT patent application serial number PCT/US12/27402 filed Mar. 2, 2012 by Stryker Corporation, and entitled SENSING SYSTEM FOR PATIENT SUPPORTS. In addition to, or in lieu of, sensing vital signs, this pressure sensing mat is also able to detect the overall shape of the patient or object positioned on the mattress. This overall shape is processed by either controller 56, or a controller within the flexible pressure sensing mat, to determine whether the shape corresponds to a human or an object. The result of this determination is used by controller 56 at step 142 to distinguish between the objects and humans moving onto or off the patient support apparatus.

In yet another embodiment, the additional sensors used at step 142 include one or more near field transceivers incorporated into patient support apparatus 20 or 20a that are able to communicate via near field communication with near field tags worn by patients or caregivers, or which are attached to equipment. If the tags are worn by patients, controller 56 is able to easily detect via this near field communication whether or not the patient is the same or a new patient. If the tags are attached to equipment, then controller 56 may be able to use the ID in that tag to identify the equipment, and therefore use that identification in the weight event log. Examples of near field transceivers that may be incorporated into patient support apparatuses and used to detect patient, caregiver, and/or equipment ID tags is disclosed in commonly assigned U.S. patent application Ser. No. 13/802,992, filed Mar. 14, 2013 by applicants Michael Hayes et al., and entitled COMMUNICATION SYSTEMS FOR PATIENT SUPPORT APPARATUSES, the complete disclosure of which is hereby incorporated herein by reference. Still other types of sensors that detect other patient or object information may be used and processed at step 142.

After completing step 142 (if any additional sensors are available), controller 56 proceeds to step 122 where it characterizes the weight event based on the analyses carried out in steps 120, 138, 140, and 142. The characterization is then presented to the caregiver for confirmation/rejection at step 124, and recorded in the weight event log at step 126, in the same manners as have been previously described above.

While the foregoing descriptions of measurement subsystems 54 and 54a have described a patient exit and/or entry event as merely corresponding to a generic patient, measurement subsystems 54 and/or 54a can be modified to distinguish between new patients that are entering the patient support surface 28 for the first time, and old patients that have previously been on the patient support surface 28. More particularly, step 122 of algorithms 114, 114a, and/or 114b can be modified to include the sub steps identified collectively as step 122a set forth in FIG. 13. It will therefore be understood that step 122a in FIG. 13 can replace step 122 in any of algorithms 114, 114a, and/or 114b.

Figure 13:
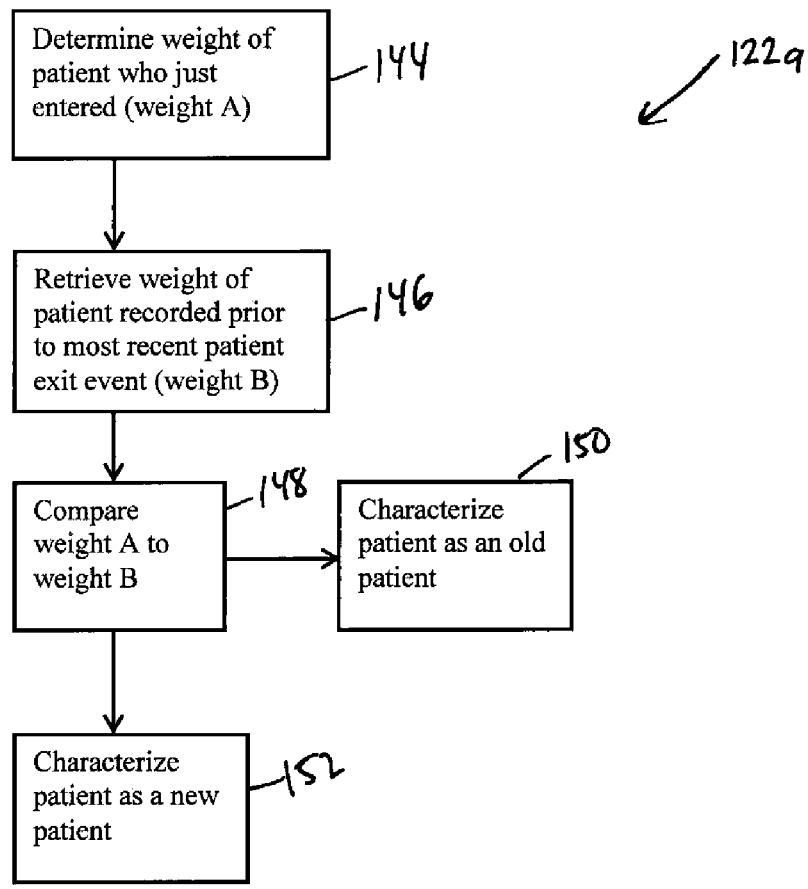
FIG. 13 is a flowchart of a first modification that may be made to one of the steps in the identification algorithms of FIG. 9, 11, or 12.

Step 122a of FIG. 13 begins at a sub step 144 that is only invoked if controller 56 has previously determined that a weight event corresponds to a patient entering patient support surface 28. In other words, step 122a is not invoked if controller 56 determines that a weight event corresponds to an object being removed from, or added, to patient support surface 28, or if it corresponds to a patient exiting patient support surface 28. During sub step 144, controller 56 determines the weight of the patient (or other person) who has just entered patient support surface. This weight has been arbitrarily labeled "weight A" in FIG. 13. This weight determination takes place automatically in the manners described above (that is, it includes any zeroing out of weights detected by load cells 36 that do not correspond to patient weight).

After controller 56 has determined at sub step 144 the weight of the patient who has just entered onto patient support surface 28 (weight A in FIG. 13), controller 56 moves to sub step 146, where it retrieves from memory 58 the patient weight recorded moments before the most recent patient exit event (identified as "weight B" in FIG. 13). That is, as has been noted above, measurement subsystems 54 and 54a are both configured to automatically take repeated weight measurements substantially continuously and record those, or at least record any changes of significance (any series of multiple weight recordings that do not have any significant change can be stored in memory as a constant weight with a beginning and ending time in order to save memory). At sub step 146, controller 56 retrieves from memory the patient weight that was recorded at a moment preceding (either immediately, or closely preceding) the last patient exit from patient support surface (weight B). If there are no previously recorded patient exits, then the patient who just entered the patient support apparatus must be a new patient, so controller 56 skips to sub step 152 (discussed below) where it characterizes the patient as a new patient.

However, in those cases where a previous patient exit event was recorded, controller 56 retrieves the patient weight B and moves to sub step 148 where it compares weights A and B to each other. More specifically, at sub step 148, controller 56 determines the percentage of difference (if any) between weights A and B. If weight A differs from weight B by more than a threshold percentage, then controller 56 concludes that the patient who just recently entered patient support surface 28 is a patient different from the one who previously occupied patient support surface 28, and therefore corresponds to a new patient. Controller 56 therefore moves onto sub step 152 where it characterizes in the weight event log the patient entry as corresponding to a new patient. As with all entries in the weight log, the caregiver has the opportunity to confirm or reject this characterization.

If weight A does not differ from weight B by more than the threshold percentage, then controller 56 moves onto sub step 150, where it characterizes the recent patient who just recently entered the patient support surface 28 as the same patient (i.e. an old patient) who was previously occupying patient support surface 28. This characterization is recorded in the weight event log and the caregiver has the opportunity to confirm or reject it.

The threshold percentage used in sub step 148 may vary from embodiment to embodiment, but will generally be in the neighborhood of one or two percent. Such small percentage changes in weight may be due to a variety of different activities that the patient may have engaged in during the time they exited the patient support surface. Such activities include the patient removing or adding clothing, eating food, drinking liquids, and/or visiting the restroom. Any weight changes greater than this threshold will be assumed to indicate that a new patient has entered the patient support surface 28. In some embodiments, the threshold percentage may be dynamically correlated to time: that is, the longer the patient is gone from the patient support surface, the more the threshold percentage may increase, which would reflect the fact that greater periods of time away from the patient support surface would afford greater time for weight-changing activities.

Modified weight characterization step 122a therefore gives measurement subsystems 54 and/or 54a the added ability of providing greater information about the patient weight events by being able to distinguish between old and new patients.

Modified step 122*a*, however, can be improved even further in other embodiments. That is, modified step 122*a* is still not able to distinguish between a new patient and an old patient who happen to have the same weight (or have weights that are less than the threshold of sub step 146). In order to address this possibility, characterization step 122*a* can be modified to an even greater step in some embodiments.

Figure 14:
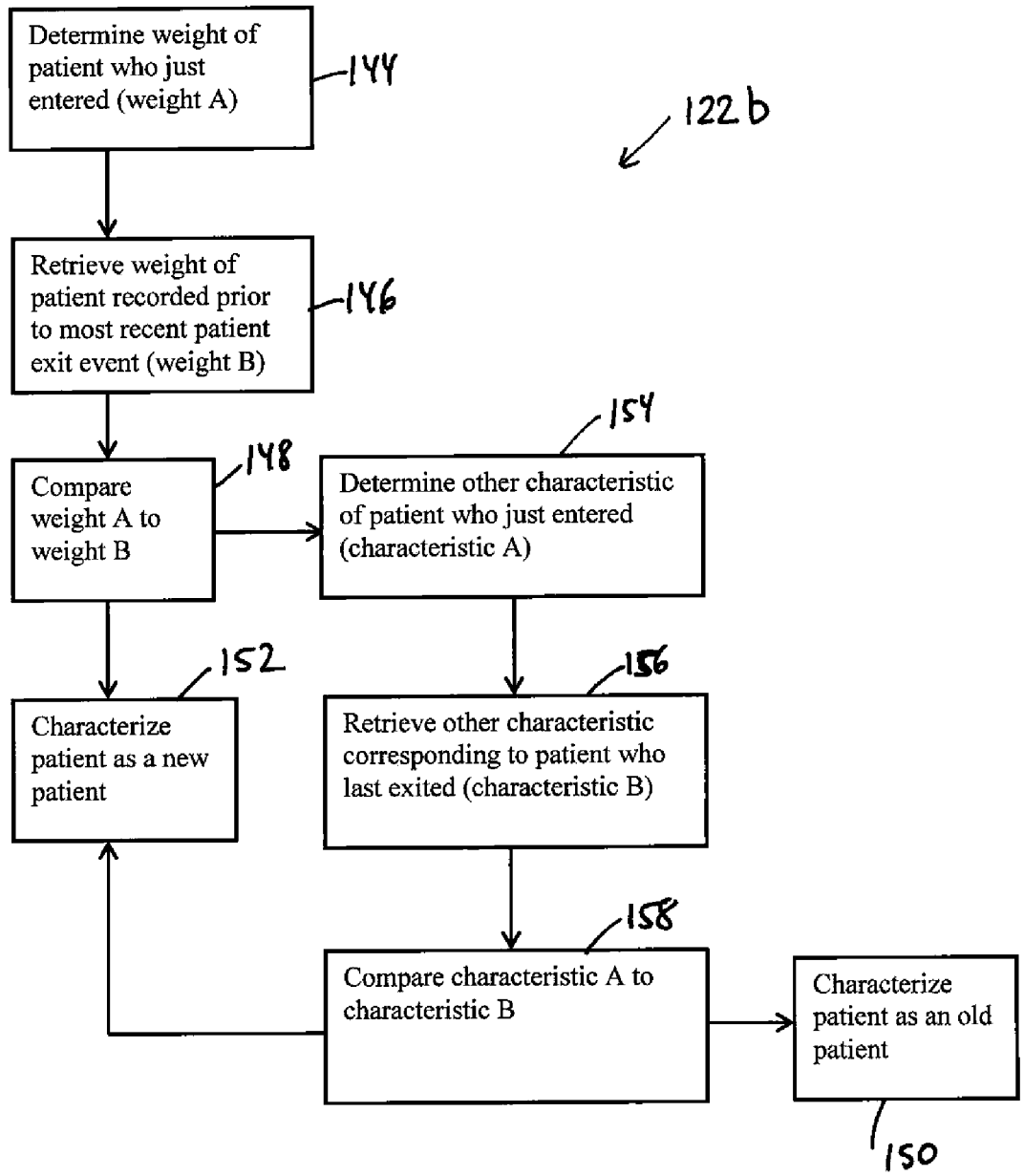
FIG. 14 is a flowchart of a second modification that may be made to one of the steps in the identification algorithms of FIG. 9, 11, or 12.

FIG. 14 illustrates another modified characterization step 122*b* that is adapted to be able to better distinguish between old and new patients who have the same, or nearly the same, weight. Modified characterization step 122*b* is useful in those measurements subsystems, such as subsystem 54*a*, where controller 56 is in electrical communication with one or more additional sensors that provide additional information about the patient. Step 122*b* of FIG. 14, like step 122*a* of FIG. 13, begins at a sub step 144 that is only invoked if controller 56 has previously determined that a weight event corresponds to a patient entering onto patient support surface 28. In other words, step 122*b* is not invoked if controller 56 determines that a weight event corresponds to an object being removed from, or added, to patient support surface 28, or if it corresponds to a patient exiting patient support surface 28.

Sub steps 144, 146, 148, 150, and 152 of modified characterization step 122*b* are the same as those sub steps of modified characterization step 122*a*, with the sole possible exception of sub step 148. Sub step 148 of step 122*b* may differ from sub step 148 of step 122*a* by utilizing a different threshold. In some embodiments, this threshold may be greater than in step 122*a*. This is because modified step 122*b* uses additional information to distinguish between old and new patients, so only greater weight changes will lead controller 56 to conclude a new patient has entered at step 152. Whether or not weight variations less than this increased threshold are the result of weight change or a different patient is resolved by sub steps 154, 156, and 158, as described below.

If controller 56 determines at sub step 148 that the weights A and B are not different by more than the threshold, it moves onto sub step 154, where it determines another characteristic of the patient who has just recently entered onto patient support surface 28. This another characteristic is determined by one or more additional sensors that are in communication with controller 56. One such additional sensor is the vital sign sensor 134 shown in FIG. 10 of measurement subsystem 54*a*. Other sensors can also be used that are coupled to controller 56 by way of an additional interface (not shown). Such other sensors could include a video camera, still frame camera, infrared sensor, or other types of sensors. Regardless of the specific sensor, controller uses the information provided by that sensor to determine a characteristic (characteristic A) of the patient who just entered the patient support surface 28.

After determining characteristic A at sub step 154, controller 56 moves onto sub step 156 where it determines the corresponding characteristic (recorded in memory 58) of the patient who last exited patient support surface 28 (characteristic B). Controller 56 then moves to step 158 where it compares characteristic A to characteristic B. If the two differ by more than a threshold percentage, then controller 56 concludes the two patients are different, and moves to step 152, where it characterizes the patient as a new patient. If the two do not differ by more than the threshold percentage, then controller 56 concludes that the same patient has re-entered patient support surface 28 and moves onto step 150, where it characterizes the patient as an old patient.

The characteristics that are used by step 122*b* in sub steps 154, 156, and 158 may vary. In one embodiment, the characteristic is a patient height. Such patient heights are able to be determined by a flexible pressure sensing mat positioned on top of, or incorporated into, a mattress positioned on top of patient support surface 28. Such mats sense the top-most pressure sensor in the array that is contacted by the patient, as well as the bottom-most pressure sensor in the array that is contacted by the patient. From this, the patient height is able to be determined. One example of such a mat that can be used with step 122*b* and measurement subsystem 54*a* to determine patient height is the mat disclosed in the commonly-assigned PCT application serial number PCT/US12/27402 filed Mar. 2, 2012 by Stryker Corporation, and entitled SENSING SYSTEM FOR PATIENT SUPPORTS, which was previously incorporated herein by reference. As was mentioned above, this type of mat is also able to detect vital signs and can be used as vital signs sensor 134. This mat can therefore serve the dual purpose of providing both vital signs and patient height to controller 56, all via the same interface 130.

As an alternative to patient height, characteristics A and B might refer to other patient distances that are measurable using a flexible pressure sensing mat of the type disclosed in the PCT/US12/27402 application. For example, instead of patient height, the flexible pressure sensing array might detect the distance between two common high pressure points on the patient's body, such as the sacrum and the patient's heels. In other embodiments, the pressure sensing mat might detect lateral patient dimension, such as dimensions characterized by the distance between the patient's shoulders, or the width of the patient's pelvis, or other measurements.

In still another embodiment, patient support apparatus 20 or 20*a* includes a near field transceiver (not shown) that is adapted to communicate with an RF ID tag, or other identification device, worn by each patient. In this embodiment, characteristic A refers to the unique number, or other characteristic, of the ID tag worn by the patient who has just returned to the patient support surface 28, while characteristic B refers to the unique number, or other characteristic, of the ID tag worn by the patient who previously had exited from the patient support surface 28. If the two numbers, or other characteristics, of the tags match, then the same patient has returned to patient support surface 28, while if the two numbers, or other characteristics, do not match, then a new patient has entered onto patient support surface 28. The integration of near field communication transceivers into patient support apparatuses for detecting, among other things, patient ID tags is disclosed in above-mentioned commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES, the complete disclosure of which has already been incorporated herein by reference.

Regardless of the specific characteristic used in step 122*b*, controller 56 stores the characteristic each time a patient enters the patient support surface. This is stored in memory 58. When a patient entry event is detected, controller 56 takes a new reading of this characteristic at sub step 154, and retrieves an old reading from memory 58 at sub step 156 (if there is no reading, then controller 56 proceeds to step 150 and characterizes the patient as a new patient). If the two characteristics are different, then controller determines that the two patients are different. If they are the same, then the controller determines that the same patient who previously occupied the patient support surface 28 has re-entered the support surface 28.

Whenever controller 56 determines that a new patient has entered the patient support surface 28, whether at sub step 152 of modified algorithm 122*a* or modified algorithm 122*b*, controller 56 is configured to notify the caregiver and prompt the caregiver to clear out any old data corresponding to the previous patient that is stored in memory 58, or any other memories contained on the patient support apparatus 20, 20*a*. Such notification may involve displaying a prompt on display 64, or it may involve issuing an aural alert, such as one or more beeps, or it may involve issuing a visual alert, such as a light or flashing light. Such notification is intended to remind the caregiver that, because a new patient has entered the patient support apparatus, any old data corresponding to a previous patient should be cleared, and new data may need to be entered for the new patient.

The old data to be cleared, as well as the new data to be entered, can take on a variety of different forms, and will vary from patient support apparatus to patient support apparatus, as well as from healthcare facility to healthcare facility. In general, however, such data may include the patient's name, height, weight, BMI, bed sore risk (e.g. Braden scale), fall risk, infection risk, and other sorts of data. If the caregiver confirms that a new patient has entered the bed, then controller 56, in some embodiments, is programmed to automatically clear the old data corresponding to the old patient from the memory (or memories) on board the patient support apparatus. In other embodiment, controller 56 merely reminds the caregiver to clear this memory, but does not do this clearance automatically. Still further, controller 56 is programmed to remind the caregiver to enter this new information whenever it determines that a new patient has entered the patient support apparatus.

Another feature of measurement subsystems 54 and/or 54*a* is the ability to characterize whether a patient supported on patient support apparatus 20, 20*a* is sleeping or not. When this feature is included within subsystems 54 and/or 54*a*, controller 56 may be programmed to consider sleeping an event that is listed in the patient weight logs. Alternatively, when a patient has fallen asleep, as well as the beginning and ending times of such sleep, may be recorded and displayed via different manners than the weight logs. Regardless of where the sleeping records are stored and/or displayed, measurements subsystems 54 and/or 54*a* are configured to determine whether a patient is sleeping by monitoring the heart rate and respiration rate of the patient and analyzing those signals to determine the sleeping or waking state of the patient. In other words, measurement subsystems 54 and/or 54*a* use one or more vital sign sensors 134 to determine whether a patient is asleep or not, and to record the times when the patient is awake and the times when the patient is asleep.

The characteristic changes in a person's breathing rate and heart rate during sleep are known in the art and do not need to be described in detail herein. Generally speaking, however, the breathing rate becomes more regular during sleep and the heart rate is reduced. The patient's temperature also decreases. Consequently, in addition to the respiration and heart rate, measurement subsystem 54 and/or 54*a* can also include communication between controller 56 and one or more temperature sensors. Regardless of which specific sensors are used, however, controller 56 makes a determination that a patient is asleep or awake and records that for viewing by the caregiver.

Figure 15:
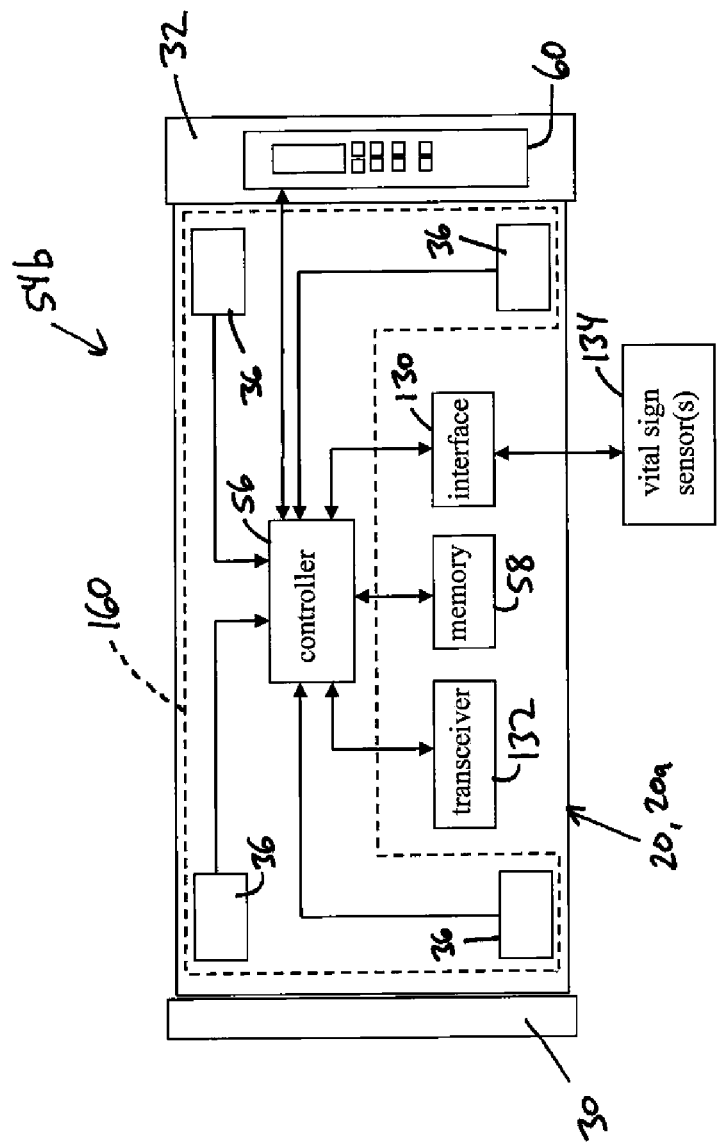
FIG. 15 is a plan view diagram of a third measurement subsystem that may be incorporated into either of the patient support apparatuses of FIG. 1 or 2.

FIG. 15 illustrates another embodiment of a measurement subsystem 54*b* that may be incorporated into either of patient support apparatuses 20 or 20*a*. Those components of measurement subsystem 54*b* that are different from subsystems 54 or 54*a* are labeled with different reference numbers, while those components that are the same are labeled with the same reference numbers. Measurement subsystem 54*b* differs from measurement subsystems 54 and 54*a* in that it explicitly includes an exit alert system 160. Exit alert system 160, in the illustrated embodiment, includes controller 56 and load cells 36. Exit alert system 160 is adapted to issue an alert when a patient has exited, or is about to exit from the patient support surface 28. In some embodiments, exit alert system works by monitoring a patient's center of gravity and issuing an alarm if the patient's center of gravity moves outside of a predefined zone, such as described in the exit system disclosed in the commonly assigned U.S. Pat. No. 5,276,432 issued to Travis and entitled PATIENT EXIT DETECTION MECHANISM FOR HOSPITAL BED, the disclosure of which has already been incorporated herein by reference. In other embodiments, exit alert system is modified to include multiple zones of different dimensions, and a caregiver is allowed to select which zone the patient's center of gravity has to move beyond before an exit alert is issued. Still other forms of exit alert systems 160 are possible.

In addition to including exit alert system 160, measurement subsystem 54*b* also differs from measurement subsystems 54 and 54*a* in that it includes the ability to automatically re-arm the exit alert system 160 after a patient returns to patient support apparatus 20 or 20*a*. Measurement subsystem 54*b* accomplishes the automatic re-arming of exit alert system 160 by recording when the exit alert system 160 is turned on and when a patient exits, or otherwise moves in a manner that causes the exit alert system 160 to issue an alert. Thereafter, subsystem 54*b* monitors the load cells 36 (and/or the vital sign sensors, or additional sensors, if the support apparatus is equipped with them) to determine when the patient returns to the patient support surface 28. When the patient has returned, controller 56 of subsystem 54*b* is configured to automatically re-arm the exit alert system after a threshold amount of time has passed since the patient re-entered the support surface 28. The threshold amount of time may vary. In one embodiment, it is of the order of ten to twenty seconds. Other thresholds can be used.

Measurement subsystem 54*b* may use any of the techniques described above to determine that a patient has re-entered the patient support system. These include looking solely at the weight of the returning patient and comparing it to the patient's previous weight, as well as looking at vital signs, height measurements, patient dimension measurements, pressure sensor array measurements, and/or other measurements that enable controller 56 to determine that a patient—as opposed to a weighty object—has returned to patient support apparatus 20 or 20*a*.

Indeed, in some embodiments, controller 56 does not look at weight measurements at all, but instead relies upon vital sign signals solely. If the vital sign sensor 134 is able to once again detect vital signs after a patient has previously exited the support apparatus, controller 56 interprets this as evidence that the patient has returned to the support apparatus, and automatically re-enables the exit alert system. In one embodiment, the vital sign sensor 134 used to automatically re-arm the exit alert system is one or more of the load cells where controller 56 examines the vital signs sensed by the load cells, as opposed to the cumulate weight sensed by them. Such vital sign sensing using the load cells is disclosed in the commonly assigned U.S. Pat. No. 7,699,784 issued to Wan Fong et al. and entitled SYSTEM FOR DETECTING AND MONITORING VITAL SIGNS, the complete disclosure of which has already been incorporated herein by reference.

In addition to, or in lieu of, any of the functions of scale system auto-zeroing, weight event characterization, sleep determination, new/old patient detection, and the other features described above that measurement subsystems 54, 54*a*, and/or 54*b* are capable of, any one of these measurement subsystems may be configured to perform yet another function that will now be described. More particularly, any of measurement subsystems 54, 54a, and/or 54b may be used to perform an activity monitoring feature which will now be described. This activity monitoring function will be described in reference to FIGS. 16 and 17. In general, the activity monitoring function measures the amount of, and times of, movement and/or activity that a patient experiences while positioned on patient support surface 28.

Figure 16:
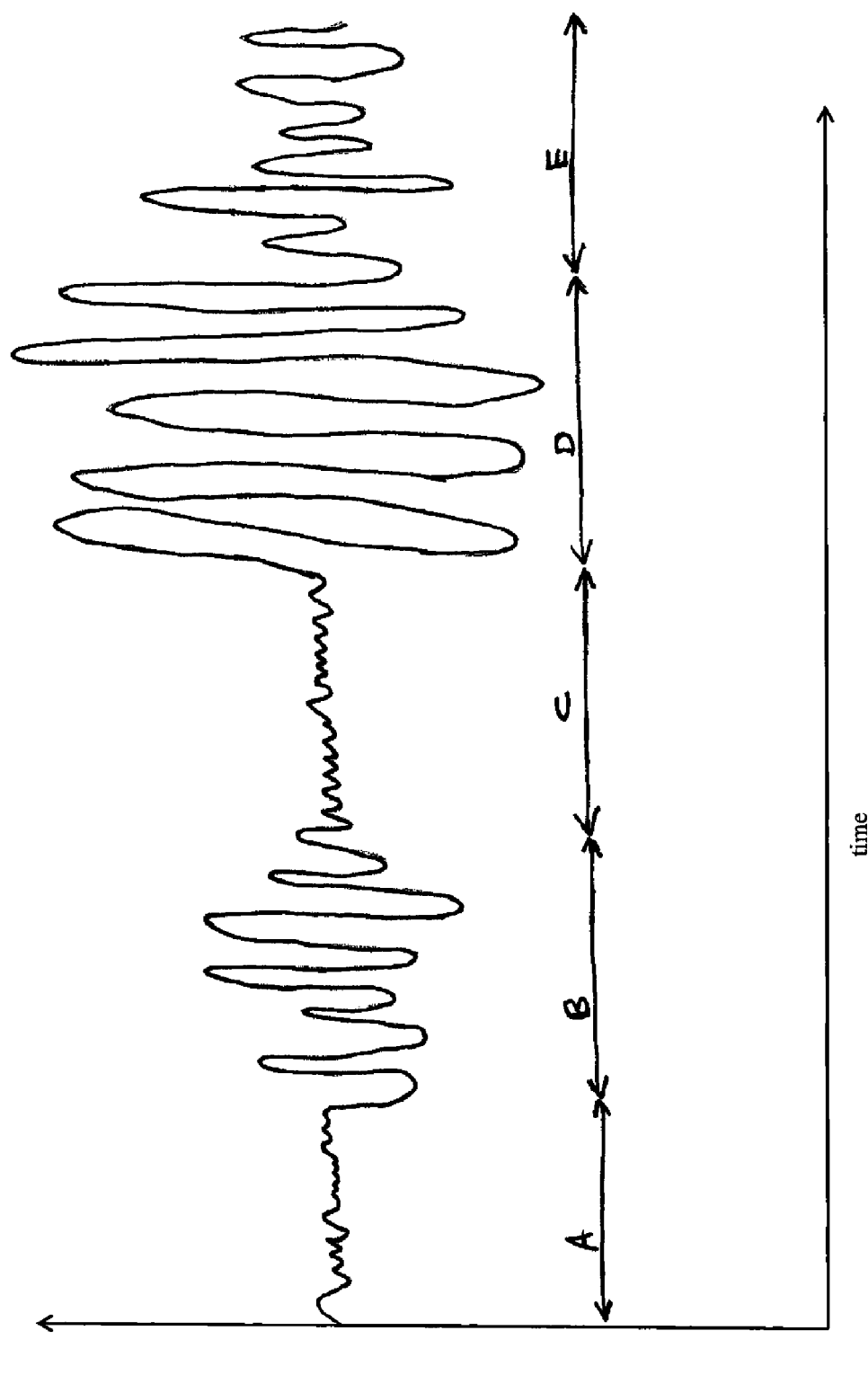
FIG. 16 is a diagram of an illustrative set of outputs that may be generated by force sensors, such as load cells, that are incorporated into any of the measurement subsystems described herein.

FIG. 16 illustrates an example of the outputs that might be generated from load cells 36 while a patient is positioned on patient support surface 28. As can be seen, the movement of the load cells varies at different periods of time. Controller 56 (in any of the measurement subsystems 54, 54a, or 54b) is adapted to characterize these various levels of movement, sum the total amount of time that a patient engages in these various levels of movement, and make that information available for display to the caregiver, and/or to forward that information to a remote location via transceiver 132. In the embodiment described herein, controller 56 characterizes the level of movement according to three different levels: low movement, medium movement, and large movement. It will be understood by those skilled in the art that different types of characterizations can be used, and that different numbers of movement levels can be used instead of the three described herein.

As shown in FIG. 16, controller 56 analyzes the outputs of the load cells 36 and breaks up their outputs into different time intervals A, B, C, D, E, etc. according to the level of movement that occurs in those intervals. Further, depending upon the level of movement that occurs in those intervals, controller 56 assigns a characterization to that level of movement. More specifically, in the example of FIG. 16, controller 56 assigns a low movement level to time interval A, a medium movement level to time interval B, a low movement level to time interval C, a high movement level to time interval D, and a medium movement level to time interval E. Further, controller 56 sums up the amount of time spent in each movement level, stores it in memory 58, and displays it on display 64 for a caregiver to look at.

The various different levels of movement are, in the example shown in FIG. 16, based on the amplitude of the load cell outputs and their variations. In other embodiments, instead of examining the load cell outputs, controller 56 is configured to examine changes in the center of gravity of the patient, as computed from the load cell 36 outputs. The levels of movement in such an embodiment are therefore based on the degree to which the center of gravity changes. The concept of categorizing the changes, however, remains the same, regardless of whether the load cell amplitudes are categorized, the center of gravity changes are categorized, or other measurements of movement are categorized.

Figure 17:
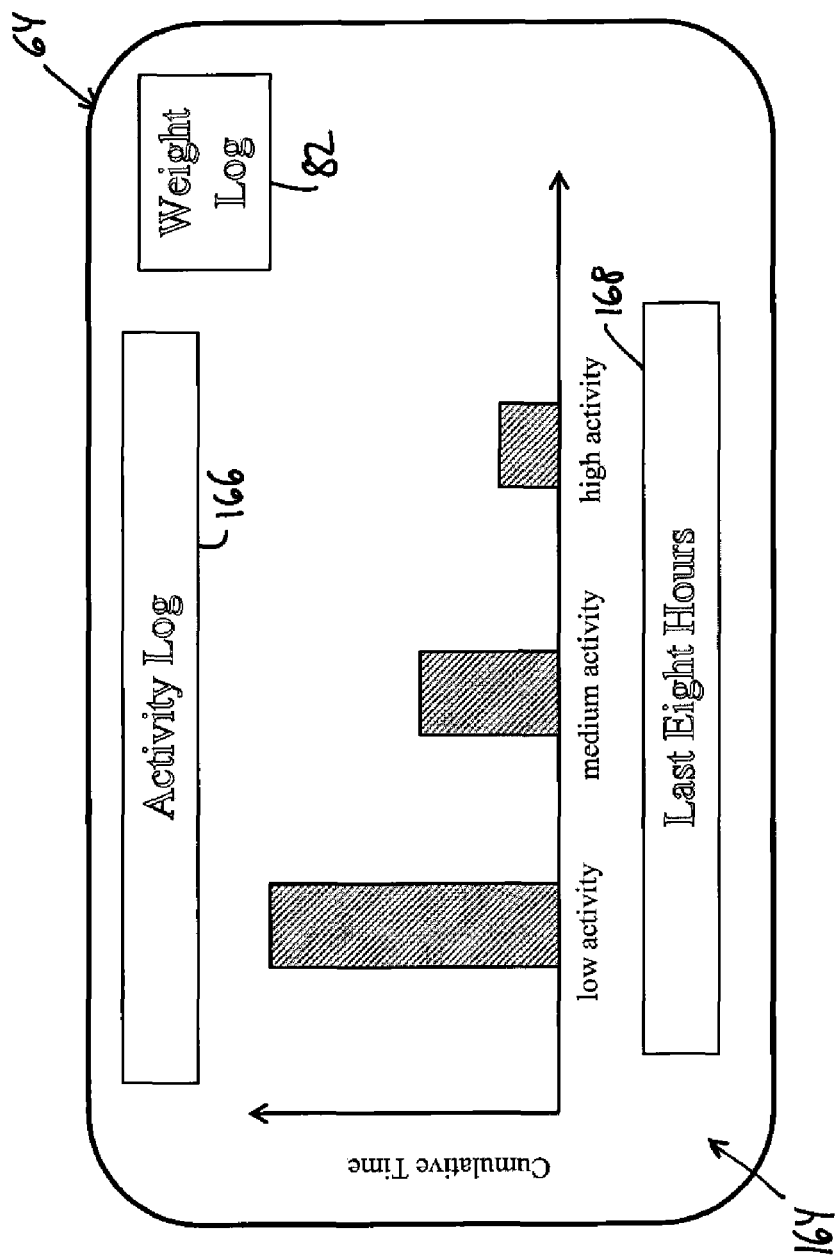
FIG. 17 is a view of an illustrative screen shot showing an activity log maintained by any of the measurement subsystems.

FIG. 17 illustrates one example of the information that controller 56 is configured to display on display 64 regarding the different levels of movement. More specifically, FIG. 17 shows an illustrative screen shot 164 of an activity log 166 that is displayable on touch screen display 64. Activity log 166 includes a bar chart having an X-axis and a Y-axis. The Y-axis corresponds to the total cumulative time (units not shown, and can vary). The X-axis corresponds to the different movement characterization levels that are available—in this example, low activity, medium activity, and high activity. The height of the different bars indicates how much time the patient has spent in each of the low, medium, and high activity states. A time range indicator 168 is included on the bottom of screen shot 164 that shows the time range corresponding to the data displayed in the bar chart. In the example of FIG. 17, the bar chart reflects the different levels of patient activity over the last eight hours. By touching indicator 168, a time range menu is displayed (not shown) that enables a caregiver to change the time range of the displayed data, including entering a custom time range. After the time range is changed, controller 56 re-computes the data for the bar graph according to the selected time range. That is, controller 56 adds up the time intervals A, B, C, etc. (examples of which are shown in FIG. 16) corresponding to each of the different activity levels, and then displays the cumulative sum for each activity level on the bar chart.

Screen shot 164 provides an easy way for a caregiver who has been away from the patient support apparatus 20 or 20a to see how active the patient has been during the caregiver's absence. This information can be useful in assessing whether the patient experienced a restful sleep or not, and/or it can be useful for determining what risk level a patient may have for developing bed sores, as well as for other purposes.

In some embodiments, screen shot 164 is modified to indicate what portions of the time displayed in the bar chart correspond to time when the patient was awake and what portions correspond to time when the patient was asleep. The manner of displaying this additional information can vary. In one embodiment, each of the bars is divided into two colors, one of which represents sleep and the other of which represent awake. Other manners of displaying this information can be used. The method for determining whether the patient is awake or not has been discussed above.

Screen shot 164 and controller 56 are further adapted, in at least some embodiments, to allow a caregiver to view the actual data on display 64 that was used to generate the bar chart. In other words, screen shot 164 and controller 56 are adapted, in some embodiments, to display the kind of data shown as an example in FIG. 16. This data provides more information to the caregiver because it indicates the times when the various levels of movement occurred, and the caregiver can therefore see if the periods of high movement were spread out, or occurred at only one or a few times, or otherwise analyze the data.

Figure 19:
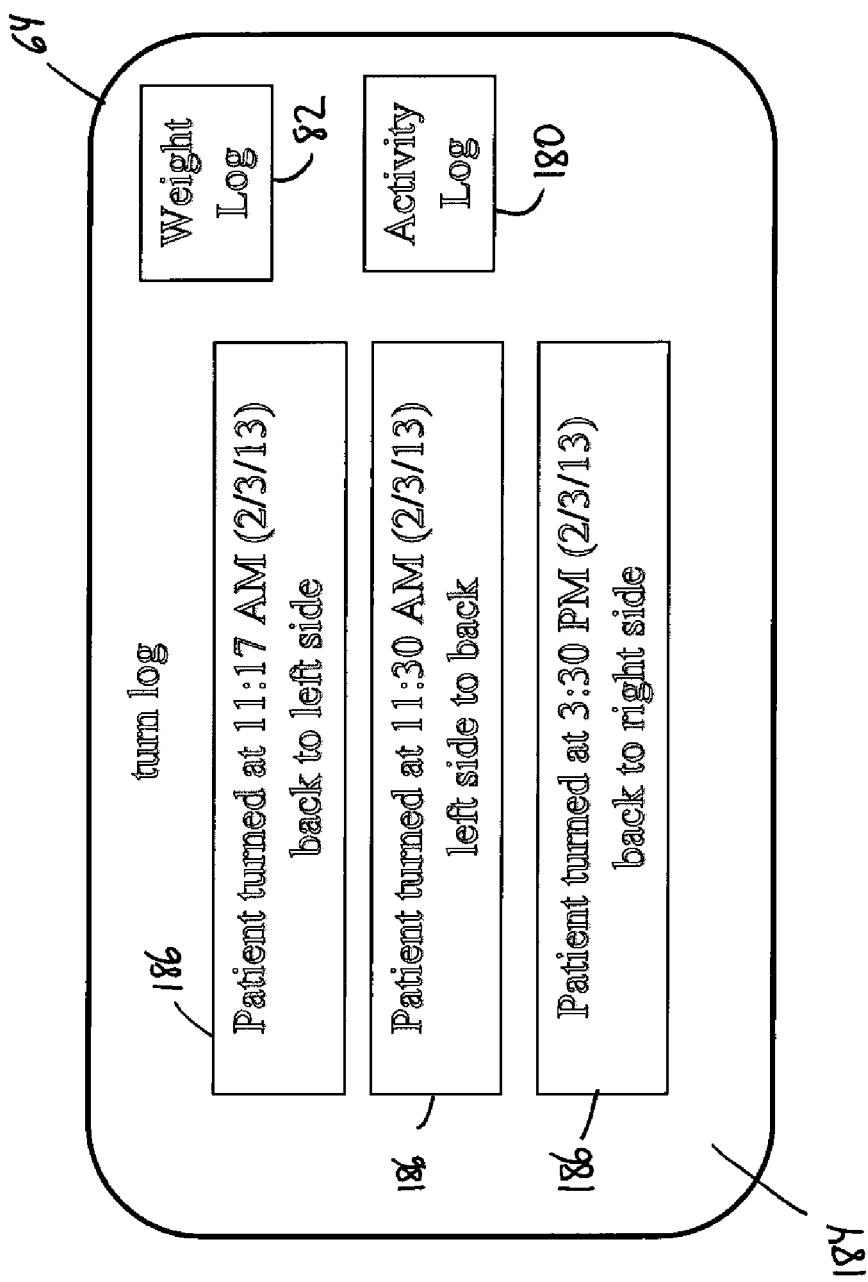
FIG. 19 is a view of an illustrative screen shot showing a turn log that may be maintained by any of the measurement subsystems.

Screen shot 164 also includes a weight log icon 82 (FIG. 17). This is included merely for illustrative purposes, and is not intended to indicate that the activity log shown in FIG. 17 is in any way dependent upon having a weight log feature in the same measurement subsystem. Some embodiments of patient support apparatus 20 or 20a include only a weight log feature, while other embodiments include only an activity log feature, while still other embodiments combine them both. If such a weight log feature is included in a patient support apparatus that also includes the activity log, then a weight log icon 82—such as that shown in FIG. 17—may be included in screen shot 164 to allow a caregiver to view the weight log by pressing on weight log icon 82. Similarly, the screen shots showing the weight log information (e.g. FIGS. 4-8 may be modified to include an activity log icon (one example of which is shown in FIG. 19 by activity log icon 180) that, when pressed, brings the caregiver to screen shot 164. In still other embodiments, the weight log and activity log information may be combined into a common log.

In addition to, or in lieu of, the measurement of different movement levels summarized above, measurement subsystems 54, 54a, and/or 54b can also be also programmed, in some embodiments, to issue an alert when controller 56 determines that a patient's movement level is so low that a patient's risk of developing bed sores has increased. In such embodiments, controller 56 examines two criteria: movement amounts and time. If the patient's level of movement has not exceeded a threshold for a specific amount of time, then controller 56 issues an alert, such as a visual alert on display 64, or an audio alert, or a flashing light, or a remote alert via transceiver 132. The threshold levels of movement and time can be predetermined and set by the manufacturer of the patient support apparatus 20 or 20*a*, or they can be programmed to be configurable by the caregiver. Indeed, in some embodiments, controller 56 will automatically set both the time and movement thresholds based upon bed sore risk assessment information that a caregiver inputs into patient support apparatus 20, 20*a*, or that is otherwise communicated to patient support apparatus 20, 20*a* (such as via transceiver 132). Such information includes Braden scale scores, or other bed sore risk assessments.

In still other embodiments, any of measurement subsystems 54, 54*a*, and/or 54*b* may be modified to include a patient turn recognition feature. When equipped with such a patient turn recognition feature, controller 56 automatically records the times when a patient is turned and makes this information available for display and/or for transmission (via transceiver 132) to electronic medical records, or other applications in communication with the healthcare Ethernet (or other communication network).

Figure 18:
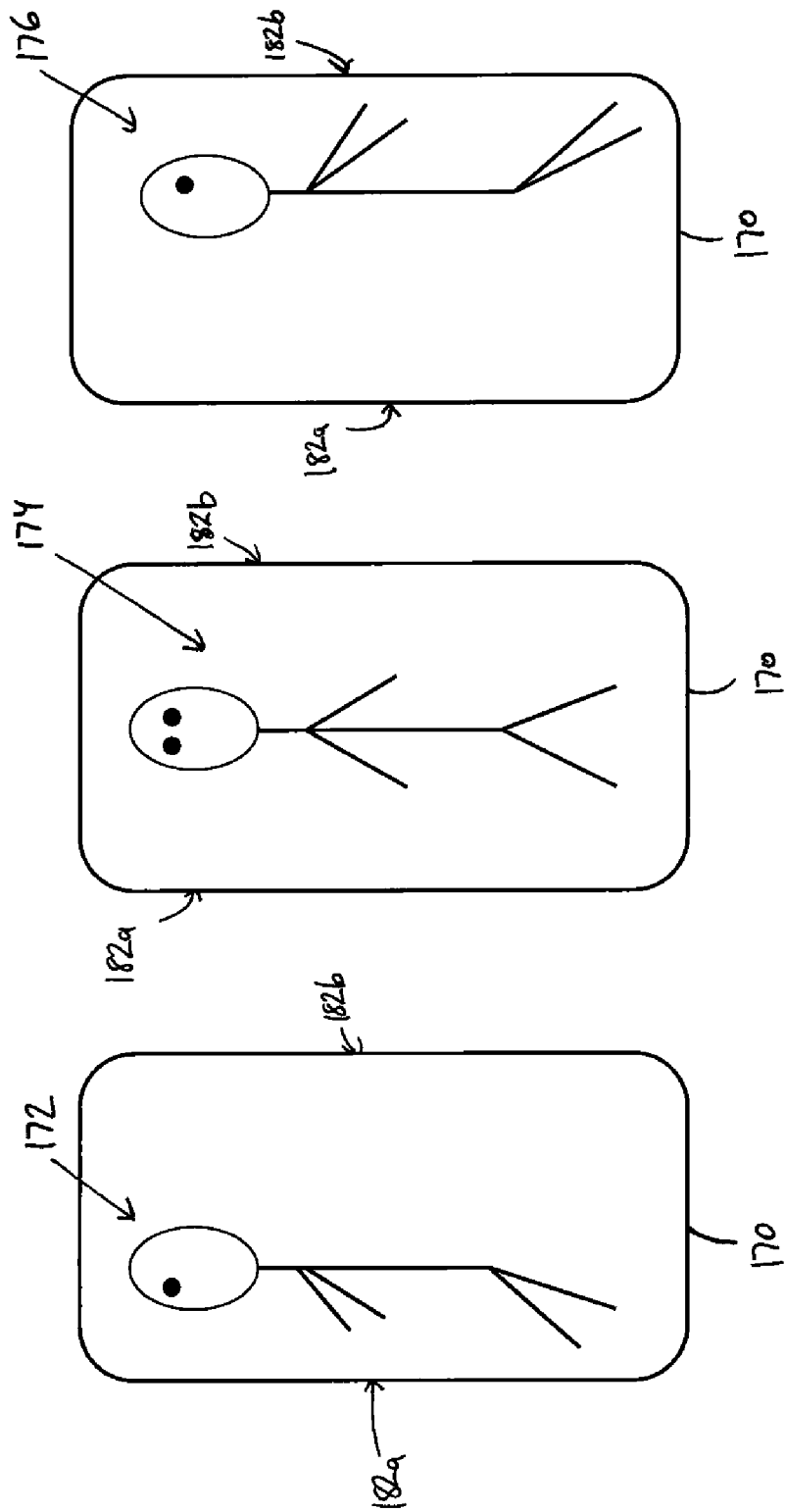
FIG. 18 is a plan view diagram illustrative three general positions in which a patient may be positioned on the patient support apparatus.

The patient turn recognition feature is an automatic feature implemented by any of the measurement subsystems wherein the load cells, or other sensors, are used to automatically detect when a patient turns while positioned on patient support surface 28. As shown in FIG. 18, a patient may rest on a mattress 170 supported on patient support surface 28 by lying on his or her right side—as indicated by position 172—or he or she may be lying on his or her back—as indicated by position 174—or he or she may be lying on his or her left side—as indicated by position 176 (it is rare for a patient to be lying on his or her stomach). The patient turn feature automatically detects which position 172, 174, or 176 the patient is in, automatically records the time at which a change in these positions occurs and the type of change (e.g. back to right side, back to left side, left side to back, or right side to back), and automatically records the amount of time that a patient spends in each different position. This information is made available for caregiver viewing on display 64 and/or it is transmitted to one or more servers or applications running on the healthcare computer network via transceiver 132.

The patient turn recognition feature differs from prior art turn recordation systems in that the patient turning is automatically recognized by measurement subsystem 54 (or 54*a* or 54*b*). In some existing patient support apparatuses, a caregiver is able to enter information into the patient support apparatus indicating that he or she has turned a patient. However, this requires manual entry by the caregiver. Further, this does not detect turns that a patient may make by himself or herself without the assistance of the caregiver. Still further, the automatic patient turn recognition feature described herein acts as a backup so that, if a caregiver forgets to enter information into the patient support apparatus indicating that a patient turn was performed, this information will nevertheless be automatically recorded. The automatic patient turn recognition feature also serves as a check to ensure that the caregiver is in fact turning the patient when he or she has indicated.

In some embodiments, the automatic turn recognition feature carried out by controller 56 is integrated into a turning protocol feature that is also present on patient support apparatus 20 or 20*a*. That is, in some existing beds, a caregiver can enter a protocol into the electronic system on the bed that indicates that the patient should be turned at a regular interval. Such a system can further issue alerts at each time interval if the caregiver does not manually enter information confirming that a turn has taken place. The automatic turn recognition feature described herein can be integrated into such a protocol system so that, if the patient turns on his or her own, the time interval is automatically reset and no alerts are issued or forwarded to the caregiver until a time period equal to the set interval passes without any turns detected. This can reduce the workload on the caregivers.

When automatically resetting any turn interval reminder, controller 56 may, in addition to looking at whether a turn has occurred or not, also look at how long the turn has lasted for. If the turn does not last for longer than a threshold amount of time, then controller 56 does not automatically reset the turn alert interval timer. This is because turns of very short duration are likely not sufficient to reduce the likelihood of a patient developing beds sores. Consequently, only turns that last for greater than a threshold justify automatic resetting of the turn interval reminder timer. In one embodiment, the threshold is initially set by the patient support apparatus manufacturer but is configurable by the caregiver so that it can be adjusted to a particular healthcare's health care protocols, or to the needs of a specific patient.

The patient turn recognition feature is carried out by controller 56. Controller 56 determines whether a patient has turned or not based upon the outputs of load cells 36, or other sensors that controller 56 may be in communication with. Such other sensors may include infrared sensors, cameras, ultrasonic, patient interface pressure sensors, or still other sensors. If relying solely upon load cells 36, controller 56 is programmed to monitor the center of gravity of the patient from the moment he or she enters the patient support surface 28. As can be seen in FIG. 18, when the patient is on his or her right side (position 172), the patient's center of gravity will typically be offset (in a lateral or side-to-side direction) toward a right side 182*a* of the patient support surface 28 (located underneath mattress 170). When the patient is lying on his or her back (position 174), the patient's center of gravity will tend to be near the center (laterally) of the patient support surface 28. Further, when the patient is lying on his or her left side (position 176), the patient's center of gravity will tend to be offset laterally toward a left side 182*b* of the patient support surface 28. By continuously monitoring these locations of the patient's center of gravity, measurement subsystem 54 (or 54*a* or 54*b*) is able to detect when a patient turns, what type of turn it was, and the duration of each of the turns. This information is stored in patient turn log, one example of which is shown in FIG. 19.

FIG. 19 illustrates a screen shot 184 of a patient turn log that may be kept by any of measurement subsystems 54, 54*a*, or 54*b*. Screen shot 184 is displayed by controller 56 on display 64. As can be seen, the patient turn log includes a listing of patient turn events 186 that have been detected by the measurement subsystem. In the example shown in FIG. 19, three turn events 186 are shown: one in which the patient turned from his or her back onto his or her left side; another in which the patient returned to lying on his or her back; and another in which the patient turned from his or her back onto his or her right side. While not shown in FIG. 19, screen shot 184 can be modified to include an icon, or other control, for changing the time period of turn events that are displayed thereon, similar to the time range adjustments for the weight log that can be implemented using up and down arrow icons 102 and 104 (see, e.g. FIGS. 7 and 8). In still other embodiments, controller 56 can be programmed to display, alternatively or in addition to screen shot 184, a screen shot having a bar chart of the cumulative amount of time that a patient spends in each turn position. Such a bar chart could be similar to the bar chart of FIG. 17 except that, instead of the bars identifying the cumulative amount of time spent in each different activity level, the bars would identify the cumulative amount of time spent in each different position 172, 174, and 176.

Screen shot 184 includes a weight log icon 82 and an activity log icon 180. Pressing on weight log icon 82 will cause controller 56 to switch to displaying the weight log, such as that shown in FIGS. 7 and 8, (if a weight log feature is included with the patient support apparatus). Similarly, pressing on activity log icon will cause controller 56 to switch to displaying the activity log, such as that shown in FIG. 17 (if the activity log feature is also included with the patient support apparatus). The inclusion of icons 82 and 180 on screen shot 184 is therefore not intended to suggest that any patient support apparatus having the turn recognition feature also must have both the weight logging feature and/or the activity logging feature. These three features are separate, and a patient support apparatus may include only one of these features, two of them, or all three of them, depending on the particular embodiment. Still further, in some embodiments where all three features are included, controller 56 may be configured to keep a common log that includes patient activity events, weight events, and turn events, rather than three separate logs.

It will be understood by those skilled in the art that various modifications can be made to the embodiments described herein. For example, instead of using load cells 36, other types of force sensors may be used in any of the measurement subsystems 54, 54*a*, and/or 54*b*. Still further, it will be understood that variations to the layout, content, and sequencing of the screen shots that have been described herein may be made. As one example, in addition to the information displayed thereon discussed above, any of the screen shots can be modified to include additional menu items that enable the caregiver to control other aspects of the patient support apparatus, such as, but not limited to, raising and lowering the height of the patient support surface 28, pivoting one or more sections of the patient support surface 28, turning on and off a brake, setting and/or editing one or more protocol alert timers, configuring a patient exit alert system, and/or other features. In one embodiment, touch screen display 64 includes the same or similar functionalities and screen images shown on the footboard display of the InTouch critical care bed manufactured by Stryker Corporation of Kalamazoo, Mich. Such functionalities and images are described in more detail in the InTouch Critical Care Bed Model FL27 Operations Manual published in 2012 (2131-409-001-Rev B), which is available from Stryker Corporation of Kalamazoo, Mich. and which is incorporated herein by reference in its entirety.

Still other alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A patient support apparatus comprising:
a support surface adapted to support a patient thereon;
a plurality of force sensors adapted to output signals corresponding to downward forces exerted on the support surface; and
a controller in communication with the plurality of force sensors, the controller adapted to analyze the signals to detect when a patient enters the support surface and to characterize the patient entry as an initial entry or a reentry of the patient on the support surface.

2. The patient support apparatus of claim 1 further including a display in communication with the controller, the controller adapted to provide an indication to a caregiver via the display when the controller characterizes the patient entry as the initial entry.

3. The patient support apparatus of claim 1 wherein the controller prompts a caregiver to confirm or reject the characterization of the patient entry.

4. The patient support apparatus of claim 1 wherein the controller is further adapted to prompt a caregiver to clear any prior patient data stored in a memory of the patient support apparatus if the controller characterizes the patient entry as the initial entry.

5. The patient support apparatus of claim 1 wherein, if the controller characterizes the patient entry as the initial entry, the controller is further adapted to prompt a caregiver to enter one or more of the following: a patient height, a patient weight, a patient name, a patient fall risk assessment, a patient bed sore assessment, a patient turn protocol, a patient alert setting, a patient body-mass index, and a patient infection risk assessment.

6. The patient support apparatus of claim 1 further including at least one vital sign sensor in communication with the controller, the vital sign sensor adapted to detect a vital sign of the patient when the patient is supported on the support surface, and wherein the controller uses outputs from the vital sign sensor when characterizing the patient entry as the initial entry or reentry.

7. The patient support apparatus of claim 6 wherein the at least one vital sign sensor is adapted to detect both a patient's heart rate and respiration rate.

8. The patient support apparatus of claim 1 wherein the controller determines the patient's weight from the signals and characterizes the patient entry based on whether or not the patient's weight is substantially equal to a previously recorded weight.

9. The patient support apparatus of claim 1 wherein the controller further analyzes the signals to determine if the signals are indicative of a non-human object placed on the support surface.

10. The patient support apparatus of claim 9 wherein the controller is further adapted to propose an identification of the non-human object based at least partially upon the signals from the force sensors.

11. The patient support apparatus of claim 10 wherein the proposed identification of the non-human object includes at least one of a medical device, bedding, and a pillow.

12. The patient support apparatus of claim 10 wherein the controller prompts a caregiver to confirm or reject the proposed identification of the non-human object.

13. The patient support apparatus of claim 1 further including:
an exit alert system adapted to issue an alert if a change in the patient's position exceeds a threshold; and
wherein the controller is further adapted to automatically re-enable the exit alert system if the signals are indicative of patient reentry and the exit alert system was armed prior to the patient reentry.

14. A patient support apparatus comprising:
a support surface adapted to support a patient thereon;
a plurality of force sensors adapted to output signals corresponding to downward forces exerted on the support surface; and
a controller in communication with the plurality of force sensors, the controller adapted to record the signals from the plurality of force sensors over time in order to determine multiple total weight readings, to determine if a likely event—other than the patient exiting from the support surface—has occurred with respect to the support surface has based upon a comparison of a total weight reading taken after the likely event and a total weight reading taken before the likely event, and to prompt a caregiver to confirm or reject that the likely event has actually occurred.

15. The patient support apparatus of claim 14 wherein the likely event includes any one or more of: (a) a new patient entering the support surface, (b) a prior patient re-entering the support surface, (c) a non-human object being placed on the support surface, (d) a person leaning on the support surface, and (e) a non-human object being removed from the patient support apparatus.

16. The patient support apparatus of claim 15 wherein, if the likely event is (c) or (e), the controller displays a potential identification of the non-human object.

17. The patient support apparatus of claim 14 wherein the controller is adapted to time stamp each likely event and to display a time corresponding to each likely event.

18. The patient support apparatus of claim 14 wherein the controller determines a baseline weight sensed by the sensors prior to the likely event, determines a second weight sensed by the sensors after the likely event, and displays a difference between the baseline weight and the second weight on a display supported on the patient support apparatus.

19. The patient support apparatus of claim 14 further including at least one vital sign sensor adapted to detect a vital sign of the patient, wherein the controller further uses an output of the vital sign sensor to characterize the likely event and display the characterization.

20. The patient support apparatus of claim 14 wherein the controller determines a baseline weight from the sensors prior to the likely event, determines a second weight from the sensors after the likely event, calculates a difference between the baseline weight and the second weight, and uses the difference to distinguish if a new patient has entered onto the patient support apparatus, or a prior patient has re-entered onto the patient support apparatus.

21. A patient support apparatus comprising:
a support surface adapted to support a patient thereon;
a vital sign sensor adapted to output signals indicative of a vital sign of a patient supported on the support surface; and
a controller in communication with the vital sign sensor, the controller adapted to analyze the signals to detect if a patient enters the support surface, compare the signals to previously recorded signals from the vital sign sensor, and determine from the comparison whether or not the patient previously occupied the support surface or not.

22. The patient support apparatus of claim 21 wherein the controller prompts a caregiver to confirm or reject whether the patient previously occupied the support surface or not.

23. The patient support apparatus of claim 21 wherein, if the controller determines that the patient did not previously occupy the support surface, the controller is further adapted to prompt a caregiver to enter one or more of the following: a patient height, a patient weight, a patient name, a patient fall risk assessment, a patient bed sore assessment, a patient turn protocol, a patient alert setting, a patient body-mass index, and a patient infection risk assessment.

24. The patient support apparatus of claim 21 further including a scale system in communication with the controller, the scale system adapted to measure a patient's weight while positioned on the support surface, and wherein the controller uses the measured weight when determining whether or not the patient previously occupied the support surface or not.

25. The patient support apparatus of claim 24 wherein the controller uses both the signals and the patient's weight to determine if a non-human object has been placed on the support surface.

26. The patient support apparatus of claim 25 wherein the controller is further adapted to propose an identification of the non-human object and display the proposed identification on a display.

27. The patient support apparatus of claim 26 wherein the proposed identification of the non-human object includes at least one of a medical device, bedding, and a pillow.

28. The patient support apparatus of claim 26 wherein the controller prompts a caregiver to confirm or reject the proposed identification of the non-human object.

29. The patient support apparatus of claim 24 wherein the controller uses both the signals and the patient's weight to determine if a person is leaning on the support surface.

30. The patient support apparatus of claim 21 further including:
an exit alert system adapted to issue an alert if a change in the patient's position exceeds a threshold; and
wherein the controller is further adapted to automatically re-enable the exit alert system if the patient previously occupied the support surface while the exit alert system was armed.

31. The patient support apparatus of claim 21 wherein the controller is further adapted to analyze the signals to determine whether the patient is asleep or not.

32. The patient support apparatus of claim 21 further comprising a plurality of force sensors adapted to output force signals corresponding to downward forces exerted on the support surface, and wherein the controller is adapted to classify the force signals into a plurality of different levels of patient movement.

33. The patient support apparatus of claim 32 wherein the controller is further adapted to issue an alert regarding potential bed sore development if the patient remains at a low level of movement for more than a predetermined amount of time.

34. The patient support apparatus of claim 33 wherein the controller enables a caregiver to select the predetermined amount of time.

35. The patient support apparatus of claim 34 wherein the controller records cumulative durations of time for each of the plurality of different levels of movement and allows a caregiver to select a range of time over which to display the cumulative durations.

36. The patient support apparatus of claim 21 further comprising an exit alert system adapted to issue an alert if a patient exits the support surface; and wherein the controller is further adapted to record how long the patient remains off the support surface after exiting the support surface.

37. The patient support apparatus of claim 36 wherein the exit alert system comprises a plurality of load cells and the controller records outputs of the load cells prior to, and during, exiting of the patient from the support surface.

38. The patient support apparatus of claim 37 wherein the controller uses the recorded outputs of the load cells to analyze future outputs of the load cells.

\* \* \* \* \*

UNITED STATES PATENT AND TRADEMARK OFFICE
CERTIFICATE OF CORRECTION

PATENT NO. : 9,320,444 B2  
APPLICATION NO. : 14/212367  
DATED : April 26, 2016  
INVENTOR(S) : Michael Joseph Hayes et al.

Page 1 of 1

It is certified that error appears in the above-identified patent and that said Letters Patent is hereby corrected as shown below:

In the Claims

Col. 35, Claim 14, Line 23:

"port surface has based"

should read

--port surface based--

Signed and Sealed this  
Twenty-first Day of June, 2016

Michelle K. Lee  
*Director of the United States Patent and Trademark Office*